United States Patent [19]

Greenfield

[11] Patent Number: 4,933,288
[45] Date of Patent: Jun. 12, 1990

[54] USE OF A MODIFIED SOLUBLE PSEUDOMONAS EXOTOXIN A IN IMMUNOCONJUGATES

[75] Inventor: I. Lawrence Greenfield, Albany, Calif.

[73] Assignee: Cetus Corporation, Emeryville, Calif.

[21] Appl. No.: 934,248

[22] Filed: Nov. 21, 1986

[51] Int. Cl.$^5$ .......................... C12N 1/20; C12N 1/22; C12P 21/00; C12P 21/06; C07H 15/12

[52] U.S. Cl. ................................ 435/252.3; 435/69.1; 435/69.5; 435/252.8; 435/172.3; 435/320; 935/23; 935/38; 935/48; 536/27

[58] Field of Search ................ 435/68, 70, 172.3, 253, 435/844, 320, 252.8, 252.3, 243; 935/23, 38, 98; 536/27

[56] References Cited

FOREIGN PATENT DOCUMENTS 0177343 4/1986 European Pat. Off. .
0196864 10/1986 European Pat. Off. .
8402351 6/1986 PCT Int'l Appl. .

OTHER PUBLICATIONS

Gray et al., PNAS81 (1984), pp. 2645–2649.
Kaczorek et al., Science (1984), vol. 221, pp. 835–858.
Kawasaki et al., Science (1985), vol. 230, pp. 291–296.

*Primary Examiner*—Thomas G. Wiseman
*Assistant Examiner*—Patricia Carson
*Attorney, Agent, or Firm*—Gregory J. Giotta; Albert P. Halluin; Elliott L. Fineman

[57] ABSTRACT

DNA sequences encoding proteins processable by secretion leaders in recombinant hosts are described. The DNA sequences encode the $NH_2$-terminal region of proteins that are cleaved from a secretion leader and may be secreted through the cell membrane and, if present, cell wall in some cases. Proteins encoded by the DNA sequence have an $NH_2$-terminal amino acid sequence conforming to a consensus amino acid sequence that is processable by the particular secretion leader. DNA sequences encoding a consensus amino acid sequence processable by the diphterhia toxin secretion leader are disclosed. A novel Pseudomonas exotoxin and CSF-1 having $NH_2$-terminal sequences conforming to a consensus sequence are exemplified.

12 Claims, 8 Drawing Sheets

DIPHTHERIA TOXIN STRUCTURAL GENE

FIG. 3

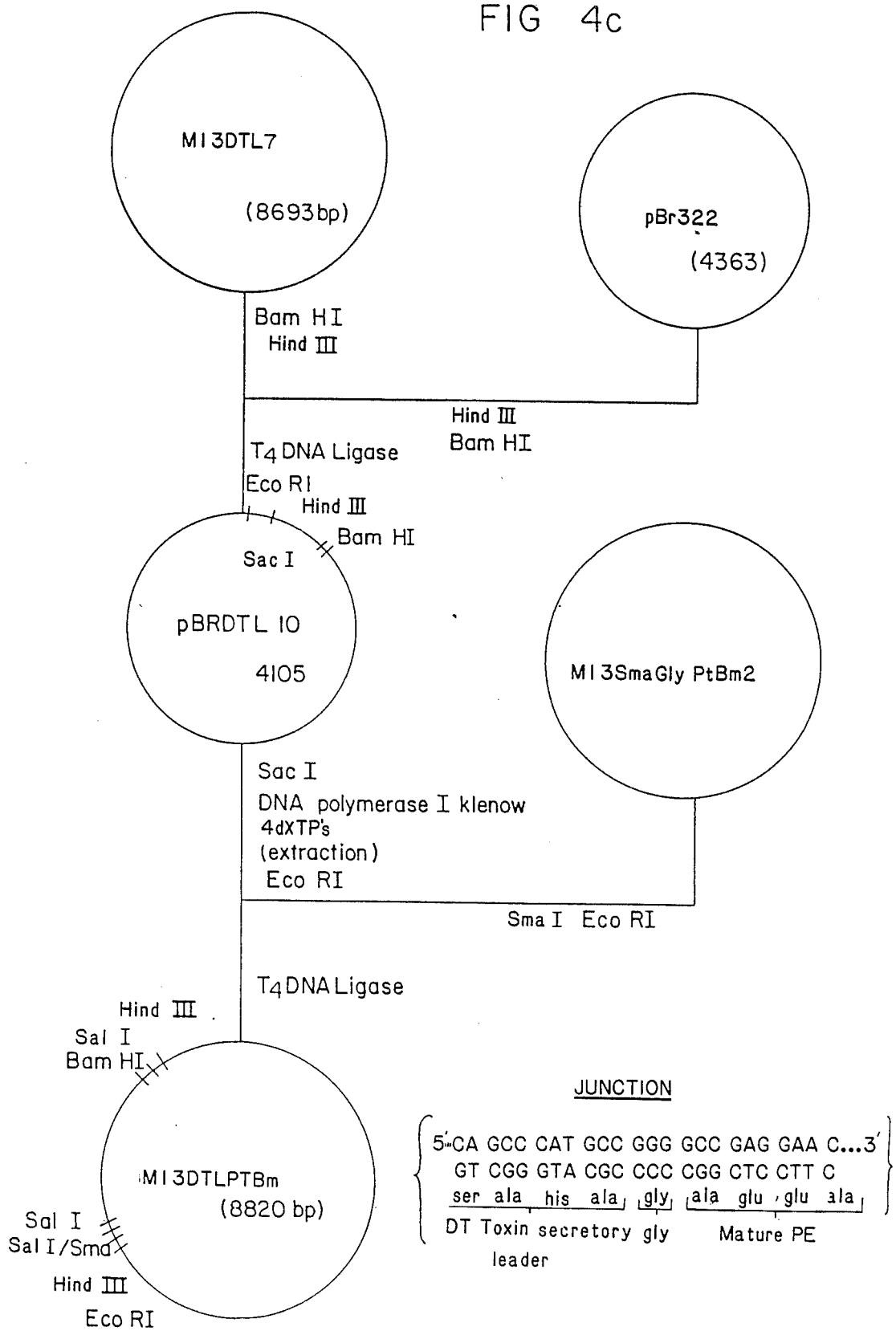

USE OF A MODIFIED SOLUBLE PSEUDOMONAS EXOTOXIN A IN IMMUNOCONJUGATES

FIELD OF THE INVENTION

The invention relates to the field of recombinant DNA technology. In particular, it relates to expression vectors for the production and processing of proteins that are heterologous to the host cell, the expression of which is controlled in part by a promoter and secretion leader that are heterologous to the protein that is expressed. The invention also concern certain modified proteins that are efficiently expressed and processed by the host cell under the control of the heterologous promoter and secretory leader.

BACKGROUND OF THE INVENTION

The expression of proteins heterologous to host cell has been accomplished with varying degree of success in a variety of host cells. For example, DNA encoding enzymes originating in the genome of one species of prokaryote have been integrated into plasmid and expressed and secreted from cells of a different prokaryotic species. Indeed, proteins originating in genera as varied as Homo sapiens, Bos, OVIS, Mus, Rattus, and others have been successfully expressed in, for example, E. coli, Saccharomyes, Streptomyces, Bacillus, and other recombinant host cells.

Notwithstanding the notable successes in, for example, the expression and secretion of insulin from E. coli as a fusion protein, the successful production and processing of proteins in association with secretion leaders is by no means a routinely achievable event. Numerous factors are entailed in the successful expression and secretion of a polypeptide in a recombinant host. The host may process certain codons encoding particular amino acids with greater fidelity than other codons encoding the same amino acid. The mRNA transcript may have the ability to form secondary structures with itself and such secondary structures may lead to decreased translation. The mRNA transcript may also form secondary structures with control sequences for the translation of the transcript such as the ribosome binding site, thereby interfering with the binding of the transcript to the ribosome and the efficient translation thereof.

After translation of the mRNA transcript has been successfully accomplished, the proper folding of the translated protein, as well as post-translational processing and secretion must also occur in order to obtain a biologically active recombinantly produced protein. Secretion, a proper folding of a protein and processing, which may be regarded as the cleavage of the mature protein from a secretion leader may be events that are separable or inseparable.

Pseudomonas exotoxin (PE) A is a powerful bacterial toxin that acts as an ADP-ribosyl transferase and inhibits protein synthesis in eukaryotic cells by catalyzing the transfer of the ADP ribosyl moiety from oxidized NAD onto elongation factor-2 (EF-2). The nucleotide sequence of PE and its cloning and expression in *E. coli* has been disclosed by Gray et al., *Proc. Natl. Acad. Sci. USA* 81: 2645–2649 (1984). Most importantly, Gray et al. report that the material so expressed is enzymatically active but is neither processed nor secreted. They suggest that all the components required for secretion of PE toxin from *E. coli* are not present in that host. Gray et al. also point out that PE and diphtheria toxin (DT) share certain characteristics including size, secretion as a single polypeptide chain having disulfide bridges and no free sulfhydryl groups, alteration in covalent structure from an inactive proenzyme to an enzymatically active state, similarity of site of enzymatic activity and maximal production in iron deficient medium. Despite these similarities, the two toxins are immunologically non-crossreactive, have different amino acid composition, differ in their mode of activation, and bind to different cell receptors. Furthermore, while intact DT binds ATP and possesses NAD glycohydrolase activity, PE lacks these properties. Lastly, computer analysis and DNA hybridization studies carried out by Gray et al. indicate no regions of significant homology between these proteins.

Mozola et al., *J. Bacteriol.,* 159: 2, 683–687 (1984) report the cloning and expression in *E. coli* and Pseudomonas of fragments of the Pseudomonas exotoxin A DNA sequence derived from the chromosomal DNA of *P. aeruginosa* strain PA103. These cloned and expressed partial sequences, while having at least partial immunological identity with Pseudomonas exotoxin A by Western blot, were from the carboxyl terminal regions of the gene encoding the toxin. Further, supporting this conclusion by Mazola et al. that the $NH_2$-terminus of the gene was not present, was the observation that the protein was not secreted. The known published literature therefore indicates that secretion of Pseudomonas exotoxin A as a cloned product in both Pseudomonas and in other hosts is unprecedented.

Immunoconjugates of Pseudomonas exotoxin are known and methods for the making thereof are disclosed in U.S. Pat. No. 4,545,985.

It would be advantageous to produce Pseudomonas exotoxin A and other proteins in processed form in a convenient host. The production of processed proteins in which a leader sequence is removed from the mature protein would confer several advantages. First, such processed proteins would lack amino acids unnecessary in the mature form for the biological activity of the protein. If the processed protein is obtained and ultimately used parenterally in a patient, the absence of leader sequence amino acids would be expected to make the mature protein less immunogenic. In addition, processing of the leader sequence and production of the mature protein clearly accomplishes, in the recombinant host, a processing step that would otherwise be carried out by other chemical or enzymatic means. Processing of the leader sequence by the recombinant host and proper secretion may also, advantageously assist in the proper folding of the expressed protein product thereby to achieve biological activity without further in vitro processing steps.

Furthermore, processing by *E. coli* as the recombinant host to form a mature proteion, eliminates the necessity of placing an $NH_2$-terminal methionine at the $NH_2$-terminus of the mature protein since the start codon ATG is found at the signal or leader sequence $NH_2$-terminus. Such $NH_2$-terminal methionine residues may be immunogenic when formed as part of a mature protein and may be chemotactic.

In addition, such in vivo processing of the precursor protein by the recombinant host is involved in extracellular secretion of the processed protein. In most Gram-negative hosts, such secretion might be expected to be periplasmic. Suh periplasmic extracellular secretion can be expected to lead to savings in the processing to remove extraneous intracellular proteins produced by the recombinant host. Surprisingly, it has been found that at least with respect to Pseudomonas exotoxin A secretion in *E. coli*, is extramural, i.e., passes through the cell wall and accumulates in the growth medium.

BRIEF DESCRIPTION OF THE INVENTION

In one respect, the invention concerns an expression vector suitable for expression of proteins in Gram-negative hosts such as *E. coli* comprising a DNA sequence encoding a diphtheria toxin secretion leader having a translation initiation signal compatible with the Gram-negative host in reading frame with a DNA sequence encoding a protein heterologous to the DT leader, said protein having an $NH_2$-terminal consensus sequence comprising gly-B, C, D, E, F, and G. B is a mildly hydrophobic amino acid C, D and G are negatively charged amino acids in aqueous solution at pH 7, and at least one of E and F is a hydrophobic amino acid.

In another respect the invention relates to DNA sequences encoding mature proteins heterologous to the DT leader that have been altered in the $NH_2$-terminal region thereof to be compatible with the DT leader whereby the DT leader is cleaved from the mature protein.

In yet another aspect the invention relates to DNA sequences encoding mature protein heterologous to the DT leader comprising an $NH_2$-terminal concensus sequence of about 7 amino acids compatible with the DT leader.

In still another aspect, the invention relates to DNA sequences encoding an amino acid consensus sequence of 7 amino acids provided that said consensus sequence is the same as the $NH_2$-terminal amino acids of DTA.

In a further embodiment, the invention relates to a mature protein having an $NH_2$-terminal region compatible with the DT leader sequence provided that the mature protein is not diphtheria toxin or an enzymatically active or inactive form of diphtheria toxin.

In yet a further embodiment, the invention relates to a mature protein having an N-terminus that has been altered to be compatible with the DT leader wherein the DT leader is cleaved from the mature protein.

In yet a further aspect, the invention relates to an amino acid consensus sequence comprising about 7 amino acids compatible with the DT leader provided that said consensus sequence does not form the $NH_2$-terminal amino acids sequence of diphtheria toxin.

In yet a still further embodiment, the invention relates to a microbial host cell transformed with an expression vector suitable for expression of proteins in Gran-negative hosts such as *E. coli* comprising a DNA sequence encoding a diphtheria toxin secretion leader having a translation start signal compatible with the Gram-negative host fused in reading frame to a DNA sequence encoding a protein heterologous to the DT leader, said mature protein having an $NH_2$-terminal sequence comprising gly B, C, D, E, F, and G, wherein B is a mildly hydrophobic amino acid, C, D and G are negatively charged amino acids in aqueous solution at pH 7 and at least one of E and F is a hydrophobic amino acid.

In a preferred embodiment, the mature protein is a modified Pseudomonas exotoxin A having in addition to the amino acid sequence of Pseudomonas exotoxin A, an $NH_2$-terminal glycine.

In another aspect of the preferred embodiment the Pseudomonas exotoxin A having an $NH_2$-terminal glycine is secreted from *E. coli* in an enzymatically active soluble form. More preferred is the soluble secreted modified Pseudomonas exotoxin A which is secreted through the cell wall of *E. coli*.

In another preferred embodiment, the mature protein is human CSF having in addition to the amino acid sequence of mature CSF-1, two additional $NH_2$-terminal amino acids glycine and alanine.

BRIEF DESCRIPTION OF THE DRAWINGS

The invention will be better understood in conjunction with the following drawings.

FIG. 1 also shows a number of fragments used in the construction of Pseudomonas exotoxin A according to the invention. Each of these fragments is designated by the nucleotide number of its ends in relationship to the PstI site. The location of various restriction endonuclease sites is also shown for some of the fragments.

Figure 3:
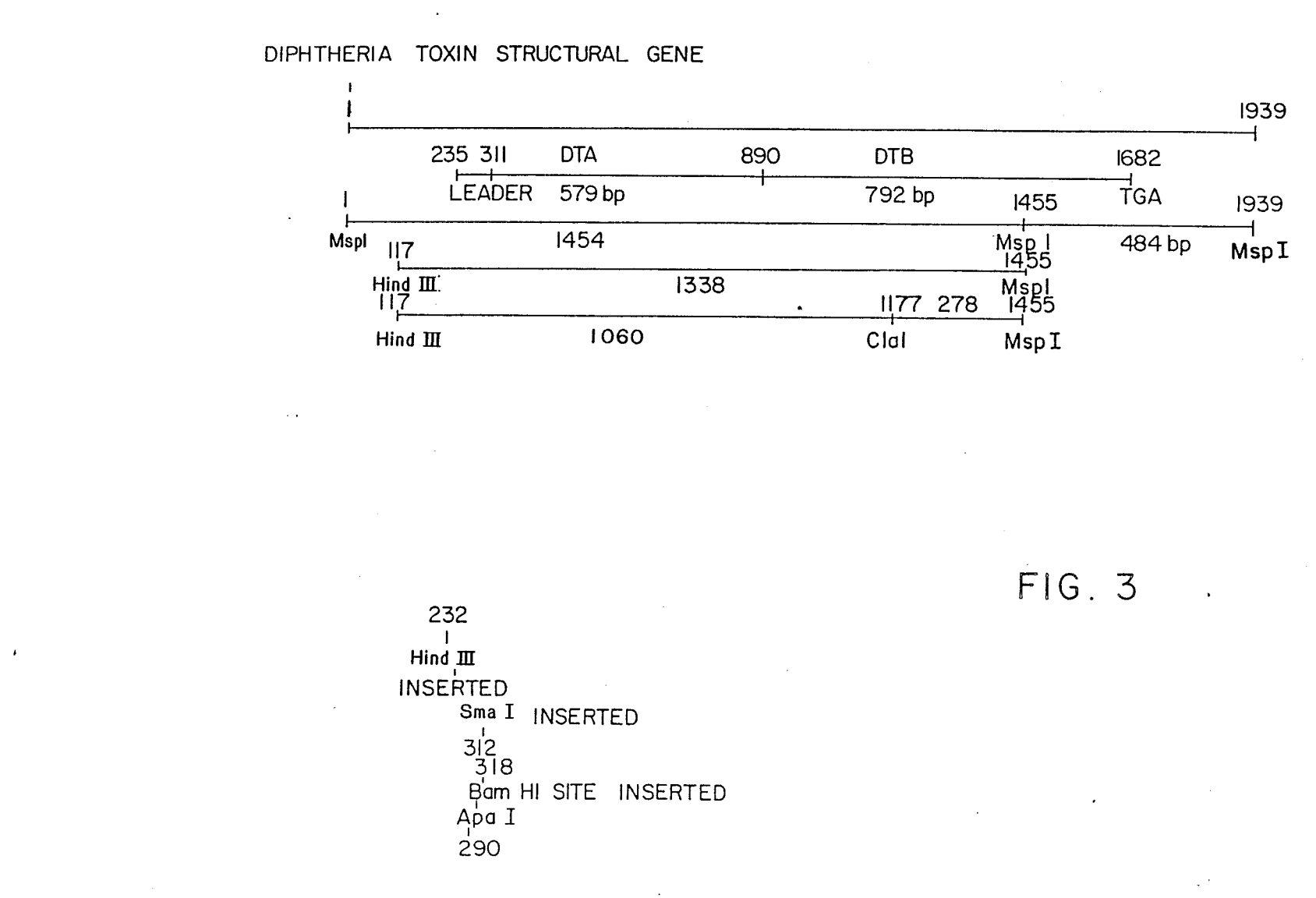

FIG. 3 is a schematic map of the diphtheria toxin structural gene. The first nucleotide of the MspI site 5' prior to the DTA leader is designated as base pair 1. FIG. 3 also shows a number of DT fragments used in the construction of the vector according to the invention. Each of these fragments is designated by the nucleotide number of its ends in relationship to the first designated MspI site.

FIG. 4 is a schematic illustration of the modifications carried out to the DT leader sequence. In FIG. 4C the mutagenized DT leader is cloned into pBR322 generating plasmid pBRDTL10. The DT leader is fused to the modified Pseudomonas exotoxin A by blunt ending the SacI site at the carboxyl end of the DT leader within pBRDTL10 followed by digestion with EcoRI, and ligation to EcoRI/SmaI digested M13SMAglyPTBM2 to form the recombinant phage M13DTLPTBM9 which therefore contains the modified DT leader and $NH_2$-terminal gly-modified mature PE in operable linkage with one another.

DETAILED DESCRIPTION OF THE INVENTION

Figure 1:
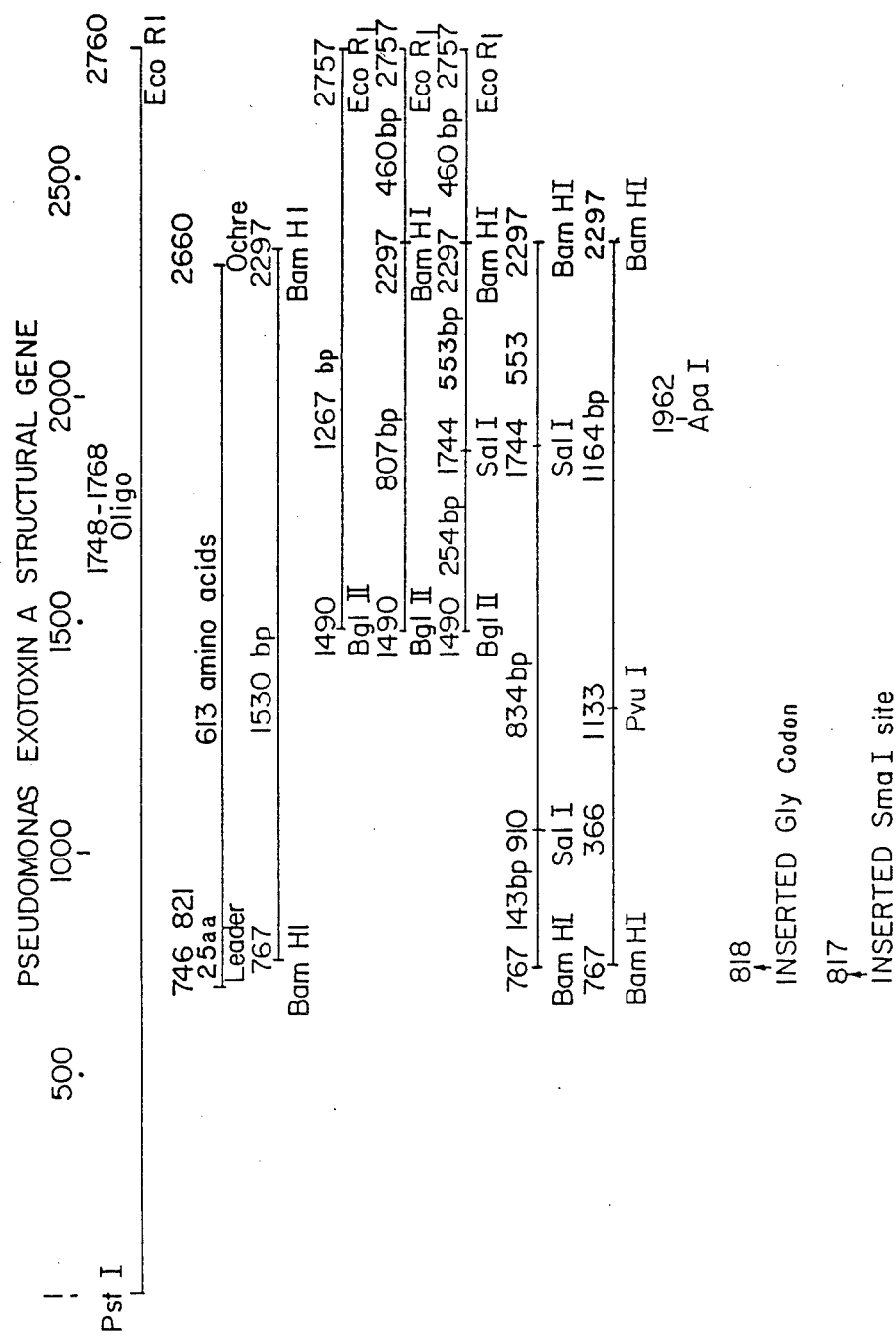
FIG. 1 is a schematic map of the Pseudomonas exotoxin A strutural gene in which the first nucleotide of the PstI site is designated as base pair 1 and the last nucleotide of the EcoRI site is designated 2760.
Figure 2:
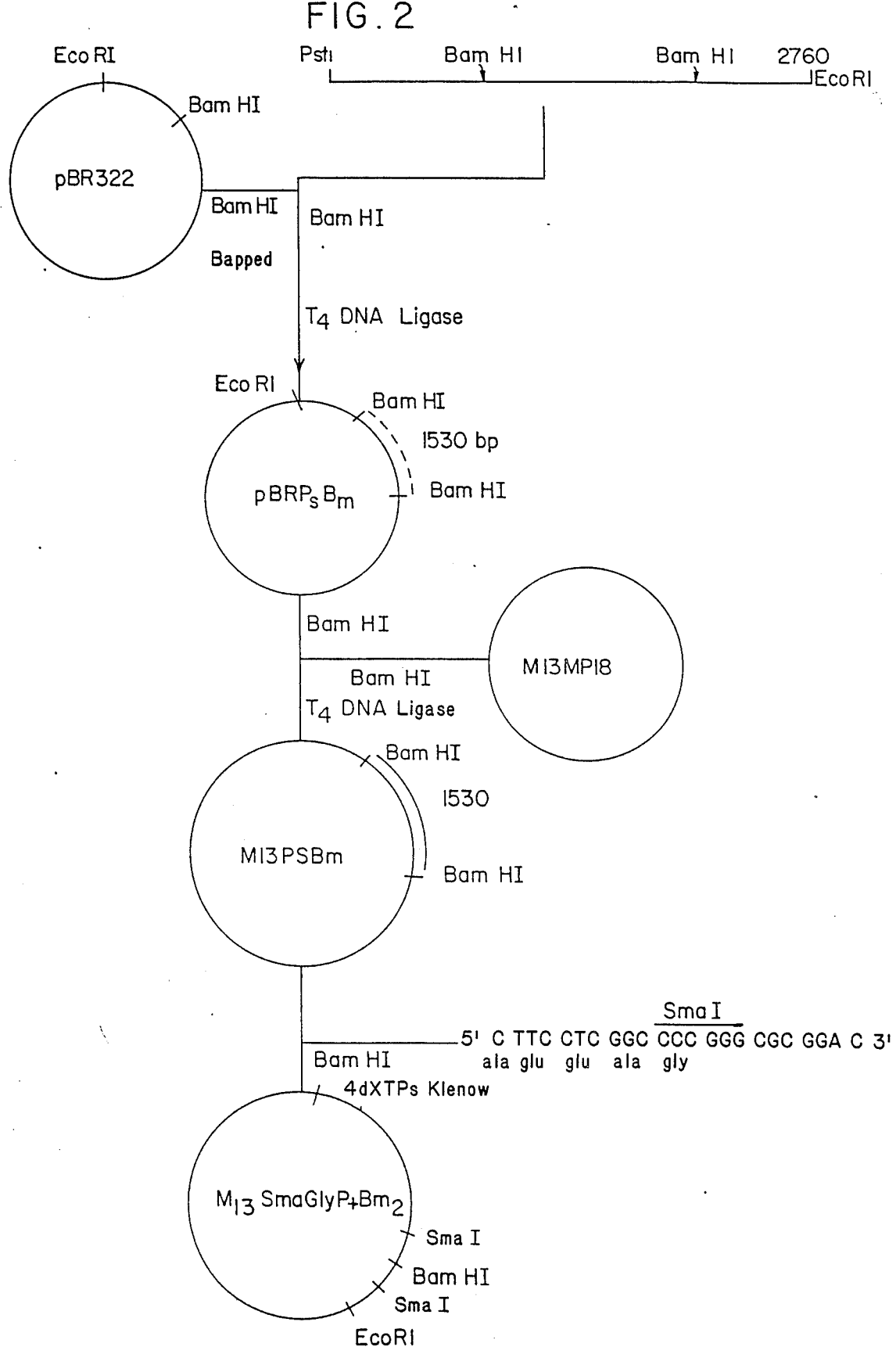
FIG. 2 is a schematic illustration of the cloning of Pseudomonas exotoxin A fragment and the creation of a glycine codon and SmaI restriction site therein by site specific mutagenesis.
Figures 4A, 4B:
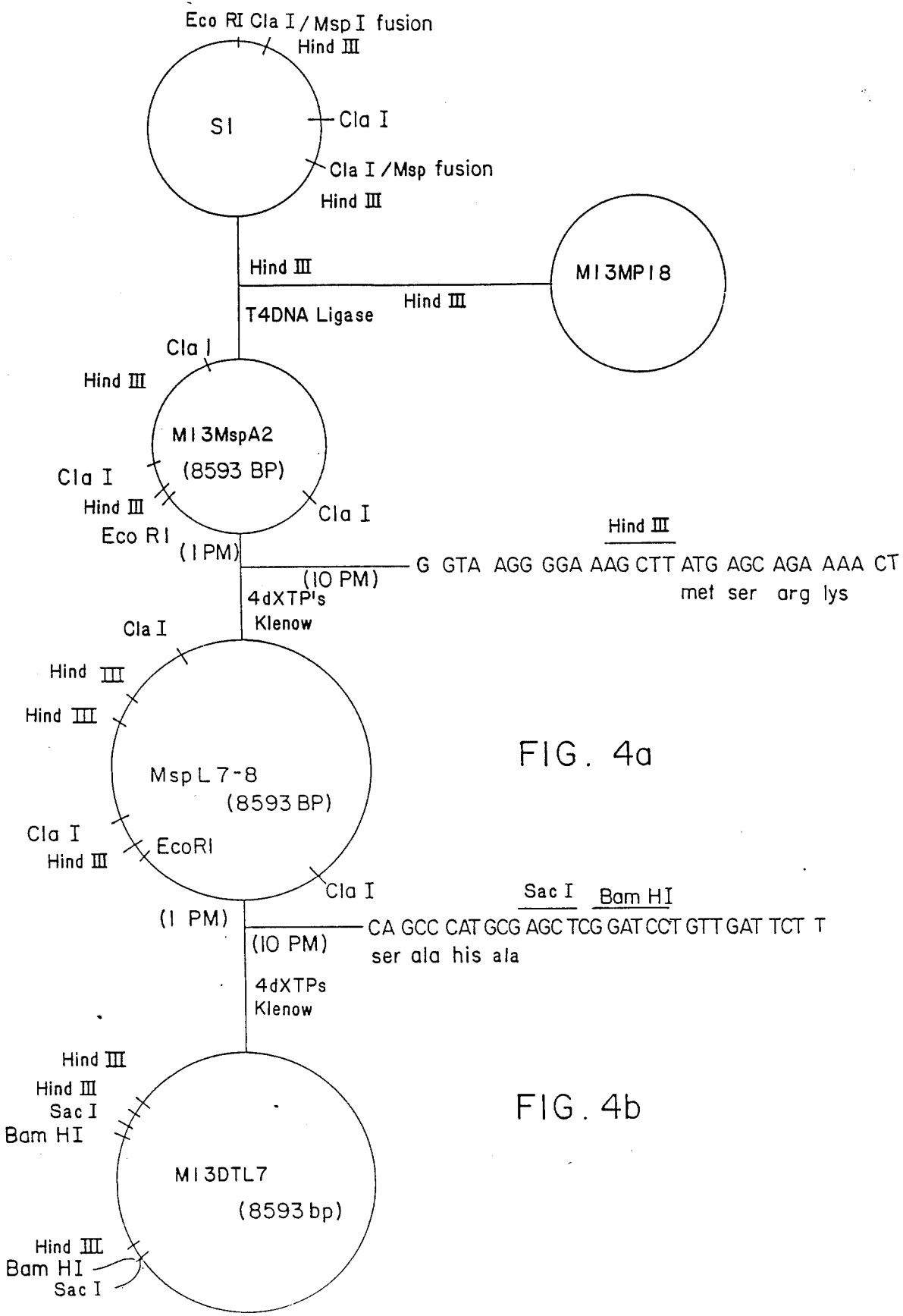
In FIG. 4A site specific mutagenesis was used to replace the GTG translation start codon with ATG and to insert a HindIII site immediately 5' to the ATG codon.
In FIG. 4B site specific mutagenesis was used to insert a SacI site for blunt end ligations to genes encoding proteins to be expressed under control of the DT leader, and to insert a BamHI site 3' to the SacI site for further cloning of the DT leader.
Figure 5:
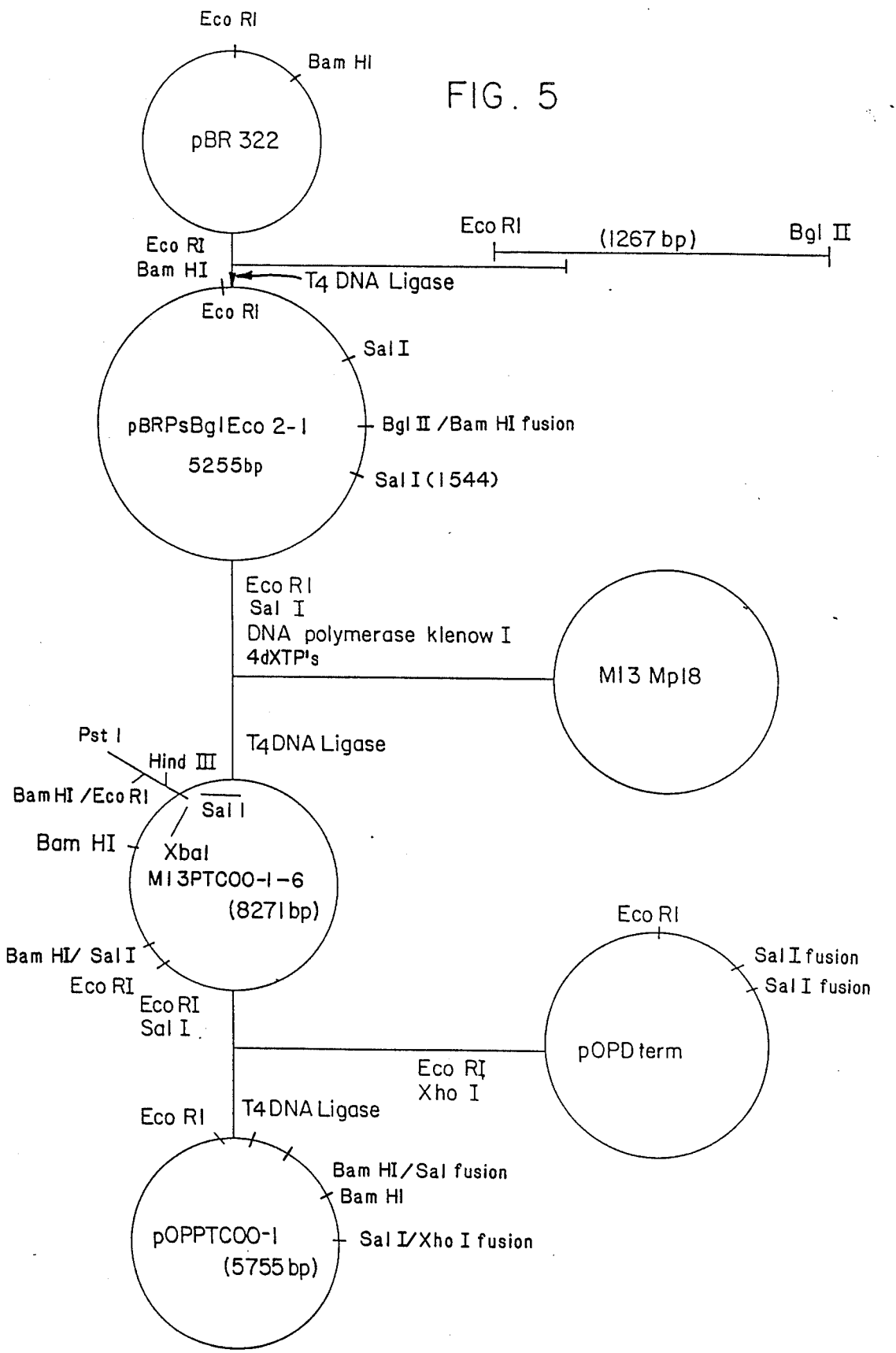
FIG. 5 is a schematic illustration of modification of the Pseudomonas exotoxin A gene to make it more convenient for cloning into a suitable expression vector.
Figure 6:
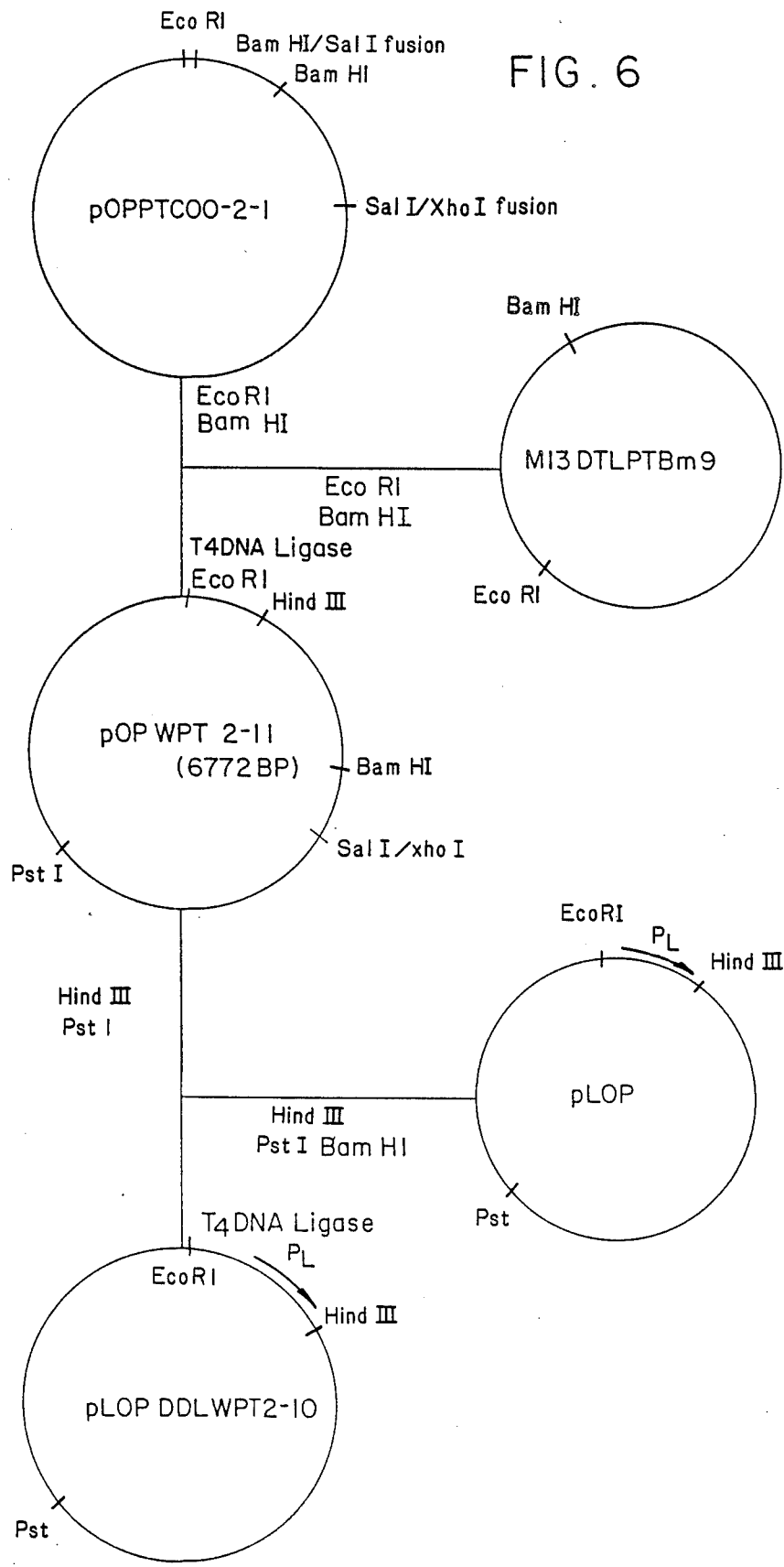
FIG. 6 is a schematic illustration of the construction of an expression vector in which the modified DT leader and $NH_2$-terminal gly-mature Pseudomonas exotoxin A gene are placed under control of the $P_L$ promoter for expression of soluble recombinant Pseudomonas exotoxin A.

General Methods for Carrying Out the Invention

Transformations

Depending on the host cell used, transformation is done using standard techniques appropriate to such cells. The calcium treatment employing calcium chloride, as described by Cohen, S. N., *Proc. Natl. Acad. Sci. (USA)* (1972) 69: 2110, or the $RbCl_2$ method described in Maniatis, et al., *Molecular Cloning: A Laboratory Manual* (1982) Cold Spring Harbor Press, p. 254 was used for procaryotes or other cells which contain substantial cell wall barriers. Infection with *Agrobacterium tumefaciens* (Shaw, C. H., et al., *Gene* (1983) 23: 315) is used for certain plant cells. For mammalian cells without such cell walls, the calcium phosphate precipitation method of Graham and van der Eb, *Virology* (1978) 52: 546 is preferred. Transformations into yeast are carried out according to the method of Van Solingen, P., et al., *J. Bact.* (1977) 130: 946 and Hsiao, C. L., et al., *Proc. Natl. Acad. Sci.* (USA) (1979) 76: 3829.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solutions. In the examples herein, typically, an excess of restriction enzyme is used to ensure complete digestion of the DNA substrate. Incubation times of about one hour to two hours at about 37° C. are workable, although variations can be tolerated. After after incubation, protein is removed by extraction with phenol/chloroform, and may be followed by ether extraction, and the nucleic acid recovered from aqueous fractions by precipitation with ethanol followed by running over a Sephadex G-50 spin column or Biogel P-4. If desired, size separation of the cleaved fragments may be performed by polyacrylamide gel or agarose gel electrophoresis using standard techniques. A general description of size separations is found in *Methods in Enzymology* (1980) 65: 499-560.

Restriction cleaved fragments may be blunt ended by treating with the large fragment of *E. coli* DNA Polymerase I (Klenow) in the presence of the four deoxyribonucleotide triphosphates (dNTPs) using incubation times of about 15 to 25 minutes at 20° to 25° C. in 50 mM Tris pH 7.6, 50 mM NaCl, 6 mM $MgCl_2$, 6 mM DTT and 5-10 µM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column or Biogel P-4. Treatment under appropriate conditions with S1 nuclease results in hydrolysis of any single-stranded portion.

Ligations are performed in 15-30 µl volumes under the following standard conditions and temperatures: 20 mM Tris-Cl pH 7.5, 10 mM $MgCl_2$, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations (5-100 nM total end concentration). Intermolecular "blunt end" ligations (usually employing a 10-30 fold molar excess of linkers) are perfomed at 1 µM total ends concentration.

Synthetic oligonucleotides are prepared by the triester method of Matteucci, et al. (*J. Am. Chem. Soc.* (1981) 103: 3185) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1-2 mM ATP, 1.7 pmoles 32P-ATP (2.9 mCi/mmole), 0.1 mM spermidine, 0.1 mM EDTA.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per µg of vector at 37° C. or 60° C. for about one hour. Vector fragments subjected to this treatment are referred to herein as "bapped". In order to recover the nucleic acid fragments, the preparation is extracted with phenol/chloroform and ethanol precipitated and desalted by application to a Sephadex G-50 or Biogel P-4 spin column. Alternatively, religation can be prevented in vectors which have been double digested by additional restriction enzyme digestion of the unwanted fragments.

For portions of vectors which require sequence modifications, site specific primer directed mutagenesis is preferred. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the single stranded phage DNA, and the resulting double-stranded DNA is transfected into a phage-supporting host bacterium. Cultures of the transformed bacterial are plated in top agar, containing susceptible bacterial, permitting plaque formation from single cells which harbor the phage. Sequence modification can also be accomplished by synthesizing the desired DNA sequence de novo from synthetic oligonucleotides as described above.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

Verification of Construction

In the constructions set forth below, correct ligations for plasmid construction are confirmed by first transforming *E. coli* strain MM294 obtained from E. coli Genetic Stock Center, CGSC 6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al., *Proc. Natl. Acad. Sci.* (*USA*) (1969) 62: 1159, optionally following chloramphenicol amplification (Clewell, D. B., *J. Bacteriol.* (1972) 110: 667). The isolated DNA is analyzed by restriction and/or sequenced by the dideoxy method of Sanger, F., et al., *Proc. Natl. Acad. Sci.* (USA) (1977) 74: 5463 as further described by Messing, et al., *Nucleic Acids Res.* (1981) 9: 309, or by the method of Maxam, et al., *Methods in Enzymology* (1980) 65: 499.

Hosts Exemplified

Host strains used in cloning and expression herein are as follows:

For cloning and sequencing, and for expession of construction under control of most bacterial promoters, *E. coli* strain MM294 (supra), Talmadge, K., et al., *Gene* (1980) 12: 235; Messelson, M., et al., *Nature* (1968) 217: 1110, was used as the host or a derivative DG98. For expression under control of the $P_L$ gene $N^{RBS}$ promoter, *E. coli* strain K12 MC1000lambda lysogen, $N_7N_{53}cI85$-$7SusP_{80}$, ATCC 39531 (hereinafter sometimes referred to as MC1000-39513) is used.

For M13 phage recombinants, *E. coli* strains susceptible to phage infection, such as *E. coli* K12 strain DG98 are employed. The DG98 strain has been deposited with ATCC July 13, 1984 and has accession number 39,768.

Definitions

1. "Compatible" as used herein with respect to translation initiation (start) signals in *E. Coli* means an initiation signal that is recognized by the ribosome of *E. coli* as the point for initiation of translation of a transcribed messenger RNA (mRNA). Based on the work of Shine and Delgarno, an ATG codon is preferred in *E. coli*. "Compatible" as used herein with respect to a mature protein in connection with a leader sequence means that the protein having the leader is processed by the host such that the mature protein is specifically cleaved from the leader sequence.

2. "In reading frame" as used herein refers to the sequential arrangment of nucleotides in sets of three that encodes the sequence of a protein without producing nonsense codons (i.e., not coding for an amino acid) or premature stop codons.

3. "Heterologous to DT leader" as used herein refers to DNA sequences encoding protein or proteins other than diphtheria toxin or fragments thereof.

4. "Consensus sequence" as used herein means a primary sequence of amino acids defining a series of positions within the consensus sequence wherein any amino acid in a particular position in the concensus sequence has certain shared characteristics with any other amino acid occupying the same position of the series.

5. By "mildly hydrophobic" is meant having a hydrophobicity correlation coefficient of at least 0.87 as described by Kubota, *J. Theor. Biol.,* 91: 350 (1981).

6. By "charged" is meant that the side chain of amino acid has a positive or a negative charge at biocompatible pH of 6–8 and high coefficient of polarity as described in Kubota, supra.

7. "Strongly hydrophobic" means having a hydrophobicity correlation coefficient of at least 1.6 as described in Kubota, supra.

8. By "mature" with respect to proteins, is meant an amino acid sequence encoding a protein free of cleaved or cleavable secretion leader sequences at the $NH_2$-terminal sequence thereof.

9. "$NH_2$-terminal" as used herein with respect to proteins means the amino terminal end of a protein with respect to the primary amino acid sequence of the protein.

10. By "microbial host" is meant in general a prokayotic host cell, preferably *E. coli* and any one of the Gram-negative microorganisms known to exchange genetic information therewith in nature or in the laboratory. A list of such naturally exchanging Gram-negative host cells is found in the Guidelines for Recombinant DNA published by the United States Government Printing Office from time to time in the Federal Register.

11. "Secreted" as used herein means that the protein or mature protein does not remain within the cytosol of the cell and may be found in the periplasmic space or outside of the cell wall in some instances.

12. "Enzymatically active" with respect to Pseudomonas exotoxin A means having the ability to inhibit the function of elongation factor 2 (EF2) as determined by covalently binding ADP ribose to EF2. The ADP-ribose-EF2 is unable to catalyse the translocation reaction of peptidyl tRNA from the A-site to the P-site on the ribosomes, causing the elongation cycle to stop.

13. "Soluble" as used herein refers to a protein that remains in the supernatant after centrifugation for 30 minutes at $100,000 \times g$ in aqueous buffer under physiologically isotonic conditions such as 0.14M sodium chloride, or sucrose at a protein concentration of as much as 10 mg/ml in the absence of detergents or denaturants.

14. "Extramurally secreted" when used in connection with secretion of proteins by Gram-negative microorganisms means that the protein may be found outside the cell wall of the intact microorganism and is usually recoverable from the growth medium.

15. "Processed" as used herein with respect to a signal or leader peptide and amino acid sequence joined thereto, means that the leader peptide is cleaved from the amino acid sequence joined thereto by the recombinant host.

Modes for Carrying Out The Invention

The invention generally concerns DNA sequences encoding mature proteins in which the mature protein is compatible with, but heterologous to a leader sequence. In the invention a DNA sequence encodes a continuous sequence of amino acids comprising a leader sequence in reading frame with a mature protein. The leader sequence is in general hetrologous to the mature protein in the sense that the mature protein is usually not found in any known host cell in nature as part of a continuous sequence of amino acids with the leader sequence. In the present invention, this situation is exemplified by a DNA sequence encoding a continuous amino acid sequence comprising the diphtheria toxin leader sequence and a sequence for the mature protein which is altered Pseudomonas exotoxin A or human CSF-1. Neither of these mature proteins is produced in any known host with the DT leader sequence. It has been found, for example, that by altering the DNA sequence encoding the heterologous mature protein within the NH$_2$-terminal region thereof, that it is possible to create a heterologous mature protein that is compatible with the leader sequence. In general, such DNA sequences encoding the mature protein, conform to a preferred sequence of amino acids that are recognized as a processing point and yield, at a minimum, specific cleavage of the altered mature protein from the leader sequence. Such preferred sequences of amino acids may be expected to differ from one leader sequence to another and from one host to another, but the requirement of a preferred amino acid sequence in the NH$_2$ terminus of mature proteins may be expected in general to render the mature protein processable by a particular leader sequence.

According to the invention with respect to the DT leader sequence in *E. coli* and strains known to exchange genetic information therewith in nature, the NH$_2$-terminal amino acid sequence of the mature protein will conform to a consensus sequence of about 7 amino acids. The consensus sequence comprises an ordered group of amino acids having characteristic hydrophobicity and polarity. This consensus sequence is exemplified by the amino acid sequences of amino terminus of mature diphtheria toxin in which the sequence is NH$_2$-gly-ala-asp-asp-val-val-asp. More broadly, the consensus sequence may be defined as gly-B, C, D, E, F, and G wherein B is a mildly hydrophobic amino acid with low polarity, C, D and G are polar amino acids, and at least one of E and F are hydrophobic amino acids with low or no polarity.

As will be seen in detail hereinbelow, the NH$_2$-terminal amino acid sequence of Pseudomonas exotoxin A, wherein this amino acid sequence has an additional NH$_2$-terminal glycine, i.e., gly-ala-glu-glu-ala-phe-asp, also falls within the 7 amino acid consensus sequence. Furthermore, the NH$_2$-terminal amino acid sequence of human CSF-1 when this amino acid sequence has additional NH$_2$-terminal glycine-alanine, i.e., gly-ala-glu-glu-val-ser-glu, also conforms to the 7 amino acid consensus sequence as defined above. The amino acid sequence of mature CSF-1 is known. See Kawasaki et al., *Science,* 230: 297–296 (1985) and U.S. patent application Ser. No. 876,810 filed June 20, 1986, the disclosures of which are incorporated herein by reference.

The consensus sequence may be further defined as follows: B has a hydrophobicity of 0.87, C D and G each have a hydrophobicity of greater than 0.60, and less than 1.0, and a polarity of at least 49, and E and F have a polarity of greater than 0 to about 1.0 and a hydrophobicity of at least about 0.85. Known amino acids having the characteristics of B include alanine. Amino acids having the characteristics of C, D and G include asp, glu, his and arg. Known amino acids having the characteristics of E and F include val, leu, phe and ile.

As described and summarized in Kubota et al., *J. Theor. Biol.,* 91: 347–361 (1981), the physical characteristics of amino acids are well known and have been tabulated according to the determinations of polarity and hydrophobicity as described in Zimmerman et al., *J. Theor. Biol.,* 21: 170. The invention thus includes a variety of DNA sequences encoding specific amino acid sequences falling within the definition of the consensus sequence. Such DNA sequence will be particularly useful when the active site of the mature protein resides in amino acid sequences that do not include the NH$_2$ terminal sequence. Thus, the consensus sequence may be created by adding a DNA sequence encoding the consensus sequence to the 5' end of a DNA sequence encoding a protein that is desired to be secreted.

The present invention also encompasses expression vectors comprising the DNA sequence encoding the DT leader sequence and a DNA sequence heterologous to the DT leader encoding the amino terminus of a mature protein compatible with the DT leader. In such expression vectors, the DNA sequence encoding the mature protein is in reading frame with the DT leader sequence and the DNA sequence encoding the consensus sequence will comprise the 5' end of the mature heterologous protein.

As mentioned above, and shown in detail hereinbelow, the consensus sequence may be constructed by site specific mutagenesis. Alternatively it may be formed by the addition of specific oligodeoxyribonucleotides in the region where the consensus sequence is required. In general, such oligonucleotide additions may be performed by digestion of the DNA with specific endonucleases followed optionally by repair and blunt or sticky end ligation to the paired oligodeoxyribonucleotide. DNA sequences encoding part or all of the consensus sequence may be inserted in this manner. Whether the DNA sequence comprising the consensus sequence is formed by site specific mutagenesis, or oligonucleotide addition and subsequent joining to the DNA sequence encoding the leader, is a matter of choice that will depend upon the number of amino acid residues required to be added, changed or deleted. The approach selected is within the choice of the ordinarily skilled person to which this art pertains.

The expression vector will generally have control sequences including promoter, ribosome binding site transcription, and translation initiation and stop signals that are operable in the particular host in which the mature protein is to be expressed. In general, the promoter and ribosome binding site will be selected to give high levels of expression at the desired time in the growth of the host cell culture. Such promoters as the trp promoter and RBS and P$_L$ promoter and gene N-ribosome binding site are inducable by trp starvation and temperature, respectively, and permit expression of the mature protein at the desired time.

As mentioned above, the translation initiation codon may be selected for maximum operability in the host cell into which the expression vector is transformed. In the case of the DT leader sequence when transformed into *E. coli*, it is preferred that the translation initiation codon be changed from GTG of the native DT leader to ATG which is the translation initiation codon preferred by *E. coli*. The host cell transformed with the expression vector according to the invention, may be selected from a variety of hosts that are known to exchange genetic information with *E. coli* in nature. Such natural exchanges are known to those skilled in the art and are listed as among those microorganisms that are exempt from the containment provisions of the Guidelines for Recombinant DNA, a volume published from time to time in the United States Federal Register.

The general principle of the invention of conforming the DNA sequence encoding at the NH$_2$-terminal amino acids of a mature protein to the NH$_2$-terminal sequence of the mature protein that normally functions with the particular leader, is applicable to a variety of host cells including a variety of prokaryotic and eukaryotic cells. In general, it is desirable to use a signal sequence that functions in the desired host cell and to carry out such alterations to the DNA sequence encoding a select mature protein that will make the N-terminus of the selected protein resemble the NH2-terminus of the protein that is produced with the particular signal protein. In the present invention, the NH2-terminal sequence of the mature protein, as exemplified, is modified so as to have a consensus sequence similar to that of mature diphtheria toxin A since the diphtheria toxin A leader is used in this instance.

The host cell, at the least, processes the continuous peptide including the leader and mature protein and cleaves the mature protein from the leader sequence. As is exemplified hereinbelow with respect to the Pseudomonas exotoxin, new and unexpected properties may arise as a result of the alterations to the amino terminal end of the mature protein. When processed by the host cell, the mature Pseudomonas exotoxin has an $NH_2$-terminal glycine added to the known Pseudomonas exotoxin amino acid sequence. Where as Pseudomonas exotoxin heretofore produced in *E. coli,* as demonstrated by Gray et al, supra, is not secreted from *E. coli;* $NH_2$-gly-Pseudomonas exotoxin according to the invention is secreted through the host cell membrane and furthermore is found in the growth medium outside of the host cell membrane. Thus, in addition to processing, the invention also entails the secretion of the altered polypeptide $NH_2$-gly-Pseudomonas exotoxin according to the invention. It will be understood is a novel protein having the unexpected characteristic being secretable by the host cell *E. coli.* Furthermore, the $NH_2$-gly-Pseudomonas exotoxin retains biological activity and may be used as the toxin component in toxin conjugates with binding moieties that selectively or specifically bind to target cells. Such selective binding moieties may include antibodies and the selective binding fragments thereof, such as F(ab) and F(ab') hormones, cytokines, such as TNF, lymphokines, such as interleukin-1 or 2, and cell growth factors such as transferrin, epidermal growth factor and bombesin. Such selective binding moieties bind to receptors found on the cells to which the selective binding molecules bind. Immunoconjugates also selectively bind to cells, however, such binding is based generally upon affinity and avidity for a particular epitope associated with the cell to which the immunoglobulin portion of the immunoconjugate binds. Thus, toxin conjugates made with the $NH_2$-gly-Pseudomonas exotoxin are intended to be within the scope of the invention.

Other proteins may be altered such that the $NH_2$-terminus is processed by the host cell in associated with the DT leader. CSF-1 as is described in detail hereinbelow, has been produced with the amino acid gly-ala added to the $NH_2$-terminus thereof, and is processed by *E. coli,* but forms aggregates.

The invention will be better understood from the following examples which are intended to be illustrative of the invention, but not limiting.

SPECIFIC EXAMPLES

Cloning of Pseudomonas Exotoxin A Gene

*Pseudomonas aeruginosa* strain PA103 was grown in liquid broth according to known methods. The chromosomal DNA was extracted, purified using CsCL-ethidium bromide density equilibrium centrifugation, and the DNA resuspended in 10 mM Tris 0.1 mM EDTA pH 8.0. The gene was then cloned in two segments (as a BamHI-BamHI fragment and a BglII-EcoRI fragment) to prevent unregulated synthesis of an active gene in *E. coli* leading to instability of the plasmid in *E. coli.*

Cloning of the BamHI-BamHI Fragment

For identification of the sequences representing for Pseudomonas exotoxin A the following synthetic oligonucleotide, encoding for positions 1748–1768 of the published sequence (Gray et al., *Proc. Natl. Acad. Sci.* (*USA*), 81: 2645 (1984)) was prepared using an automated DNA synthesizer: 5′ CAGGGCGTTGCGGATCACCTG 3′. This oligonucleotide is hereinafter referred to as LG. This 21-mer was used both in the comparison of the published map of the toxin gene with that in the current strain, as well as in identifying the desired constructions in the BamHI-BamHI and EcoRI-BglIII fragment clonings.

First, the presence of a 1530 base pair BamHI-BamHI fragment predicted from the above-indicated published sequence was confirmed for the strain used in this study. Pseudomonas chromosomal DNA was restricted with BamHI under conditions specified by the manufacturer and run on a 0.7% agarose gel. In addition, labeled DNA fragments of known molecular weights were included within the gel as markers. The DNA within the gel was nicked by treatment with 250 mM HCl, denatured by treatment with 0.2N NaOH, 0.6M NaCl and transferred to GeneScreen TM (NEN/Dupont), a microporous adsorptive membrane used for a hybridization transfer and described in U.S. Pat. No. 4,455,370 by electrophoresis. Following fixation of the DNA to the matrix by baking at 85° C. for two hours, the filter was treated in prehybridization buffer (6×SSC, 0.1% SDS, 5×Denhardt buffer, 50 mM NaP, pH 7.0, 100 μg/ml sonicated calf thymus DNA), for 4–5 hours at 42° C. The synthetic probe LG was end-labeled using T4 DNA kinase and P32-ATP, and hybridized to the filter in prehybridization buffer (using only 25 μg/ml sonicated calf thymus DNA) at 42° C. overnight. The filters were then washed at 42° C. once in 0.1% SDS, 5×SSC, twice in 0.1% SDS, 2×SSC and once in 0.1% SDS 1×SSC. Following autoradiography, the 1530 base pair BamHI-BamHI fragment was confirmed using the labeled molecular weight markers.

For cloning this fragment, a preparative amount of Pseudomonas chromosomal DNA was size fractionated on an aragrose gel. Pseudomonas chromosomal DNA was restricted with BamHI, EcoRI, and PstI (the EcoRI and PstI restriction enzymes were included to decrease the viscosity of the DNA before running on the agarose gel and do not cut within the desired BamHI-BamHI fragment) phenol extracted, ethanol precipitated and run on a 0.7% agarose gel along with molecular weight markers. Following staining of the gel with ethidium bromide, the fragments in the size range encompassing 1530 base pairs were cut out of the gel, electroeluted, run over elutip-d TM columns (Schleicher and Schuell, Inc., Keene, NH USA), and ethanol precipitated. The presence of the desired sequence was confirmed by running a small fraction of the purified size-fractionated DNA on an agarose gel, transferring to GeneScreen TM (New England Nuclear/DuPont, Boston, Mass. USA) and hybridization to the oligonucleotide probe as described above.

The size-fractionated DNA was ligated to pBR322 that had been restricted with BamHI and treated with bacterial alkaline phosphatase (hereinafter "bapped") to prevent vector self-ligation. Following transformation of the ligation mixture into E. coli strain DG98 using the CaCl₂ method of Cohen et al. (*Proc. Nat. Acad. Sci. USA*, 219: 2110–2114 (1972), ampicillin resistant colonies were grown overnight and transferred to nitrocellulose filters. The colonies on the filters were lysed using triton lytic buffer (0.2% triton X-100, 0.05M Tris, 0.0625M EDTA), the DNA denatured using 0.5M NaOH, 1M NaCl, the filters neutralized using 0.5M Tris pH 8, 1M NaCl and washed using 0.3M NaCl, 10 mM Tris pH 7.6, 1 mM EDTA. The DNA was fixed to the filters by baking at 85° C. for 4–5 hours and hybridized to end-labeled synthetic oligonucleotide LG as described for hybridizing the gel. Probe-positive clones were inoculated into liquid broth, their DNA extracted and screened for the presence of the 1530 base pair fragment by digestion with BamHI. One such clone containing the desired fragment was designated pBRPsBm and was used in subsequent steps.

Cloning of the EcoRI-BglII Fragment.

The presence of the 1267 base pair EcoRI-BglII fragment predicted in the published sequence was confirmed for the strain used in this study as described above for the BamHI-BamHI fragment except that the chromosomal DNA was restricted with EcoRI and BglIII.

For cloning, a preparative amount of size fractionated Pseudomonas chromosomal DNA was purified as described above. Pseudomonas chromosomal DNA was restricted with EcoRI and BglII according to the manufacture's specifications, and run on a 0.7% agarose gel along with molecular weight markers. Following staining with ethidium bromide, the proper size range of DNA fragments was identified using the molecular weight markers, cut out of the gel and electroeluted. This preparation was then purified by running over an elutip-d column and ethanol precipitated. The presence of the desired sequences was confirmed by running a small fraction of the purified DNA on an analytical agarose gel, transferring GeneScreen TM and probing with labeled synthetica oligonucleotide LG.

The size-fractionated DNA was ligated into pBR322 that had been restricted with EcoRI and BamHI and bapped to prevent self-ligation. The ligation mixture was transformed into E. coli strain DG98 and plated onto ampicillin containing plates. The ampicillin resistant colonies were screened for the presence of exotoxin A sequences by hybridization to end-labeled LG as described above. Probe-positive colonies were inoculated into liquid broth, grown at 37° C. and their DNA isolated using standard procedures. Since the ligation of a BglII sticky end into a BamHI sticky end destroys both restriction sites, confirmation for the presence of the desired fragments could not use digestion with BglII and EcoRI. Instead, DNA from probe-positive clones were subjected to several sets of enzymes. Digestion with the combination of BamHI and SalI was expected to yield two fragments: a 553 base pair BamHI-SalI fragment entirely within the cloned fragment, and a 530 base pair fragment consisting of SalI-BglII sequence (254 bp) within the cloned fragment, and a BamHI-SalI sequence (276 bp) within pBR322. Digestion with the combination EcoRI and SalI was expected to yield two fragments: a 1013 bp EcoRI-SalI fragment entirely within the cloned fragment, and a 530 Base pair fragment consisting of a SalI-BglII sequence (254 bp) within the cloned fragment and a BamHI-SalI sequence (276 bp) within pBR322. One plasmid having the expected restriction pattern was designated pBRPsBglEc and was used in subsequent steps.

Mutagenesis of the Sequence Encoding the Amino-Terminal End of The Pseudomonas Exotoxin A Gene There is some homology between the amino terminal ends of the mature diphtheria toxin and Pseudomonas exotoxin A with respect to charged and hydrophobic amino acids as shown below:

| PT: | Ala Glu Glu Ala Phe Asp |
|---|---|
| DT: | Gly Ala Asp Asp Val Val Asp |

Since it has been shown that the diphtheria toxin secretory leader is able to secrete diphtheria toxin in E. coli (see Greenfield et al., *Proc. Natl. Acad. Sci. USA*, 80:6853–6857 (1983)), it was reasoned that it may be able to secrete Pseudomonas exotoxin A in this host if the amino terminal end of the protein were properly aligned with the leader in a manner similar to the diphtheria toxin sequences. To this end a glycine codon (GGG) was added just prior to the first codon of the mature protein (the Ala codon). In addition, a SmaI restriction site (CCCGGG) was also added to permit easy in-frame junction to other sequences such as the diphtheria toxin leader.

Cloning the 1530 BamHI-BamHI fragment into M13.

In order to accomplish the alteration of the Pseudomonas toxin sequences, the 1530 bp BamHI-BamHI fragment described in IA above was cloned into M13MP18. M13Mp18 was restricted with BamHI and bapped to prevent self ligation. Plasmid pBRPsBM from Example IA was restricted with BamHI and PstI (the PstI was included to minimize recircularization of the plasmid), phenol extracted and ethanol precipitated. Samples of the two preparations were ligated together using T4 DNA ligase at 10° C. overnight and transformed into competent E. coli K12 strain DG98 (ATCC 39,768). The transduced cells were plated in the presence of 0.3 mM isopropyl thiogalactoside (EPC) obtained from Sigma Chemical (St. Louis, MO) and 0.3 mM X-gal on a lawn of DG98 and grown overnight at 37° C. Non alpha complimenting white plaques were grown in liquid broth and a sample of the culture was used to purify replicative form (RF) DNA. Clones in which the 1530 base pair Pseudomonas exotoxin A gene was inserted into M13MP18 in the clockwise direction were identified by restriction with SalI which resulted in two fragments: one internal 834 bp SalI-SalI fragment and a fusion 565 bp SalI-SalI fragment consisting of the 553 bp SalI-BamHI fragment from the carboxyl end of the Pseudomonas fragment linked to the 12 bp BamHI-SalI fragment in the polylinker of the vector. Further confirmation was accomplished by digestion with PvuI and PstI which yielded a 1182 bp fusion fragment consisting of the 1164 bp PvuI-BamHI fragment of the insert and the 18 bp BamHI-PstI fragment of the polylinker. The 133 bp PstI-PvuI fragment of the vector was too small to be detected on the agarose gel. Final confirmation was determined by sequencing the 3' end of the inserted fragment.

Mutagenesis of the sequence around the amino terminal end of the mature toxin.

A chemically synthesized purified 23-mer oligo deoxyribonucleotide having the following sequence (hereinafter referred to as LG20) was used to introduce a codon encoding glycine and a SmaI restriction site just prior to the alanine start codon for the mature wild-type Pseudomonas exotoxin A sequence:

```
native:      C TTC CTC GGC GGC GGA CGC GGA C

LG20:      5' C TTCCTCGGCCCC GGG CGC GGA C 3'

-ala  glu  glu  ala-(NH2)

PT position   4   3   2   1 --- gly inserted

------- SmaI restriction site
```

Because of the clockwise insertion of the Pseudomonas exotoxin A sequence in M13MP18, the sequences are complementary to the coding strand. Therefore, the inserted glycine codon (GGG) is represented in the oligonucleotide by the sequence (CCC), and the sequences encoding for the Pseudomonas exotoxin A codons are represented by their complement as shown above. The SmaI restriction site, which is part of the inserted glycine codon, allows the creation of a blunt end following restriction and permits direct fusion to desired sequences.

Approximately 10 picomoles of the LG20 were hybridized to approximately 1 picomole of single stranded DNA from clone M13PsBm in 13 μl of 10 mM Tris pH 7.4, 90 mM NaCl, 10 mM MgCl$_2$ by heating to 85° C. for five minutes followed by 45° C. for 20 minutes. The annealed mixture was chilled on ice and adjusted to 18 μl by the addition of DTT to 10 mM, each dXTP to 0.5 mM and 5 units of DNA Polymerase I Klenow fragment. The reaction mixture was incubated on ice for 20 minutes followed by incubation at room temperature for one hour. The repair reaction was then transformed into competent *E. coli* strain DG98, plated onto agar plates, and incubated overnight to obtain phage plaques.

Plaque lifts were performed off of plates containing mutagenized M13PsBm plaques as well as two plates containing unmutagenized M13PsBm phage plaques (for controls) using nitrocellulose filter circles. The filters were treated as described for the colony lifts including lysis with triton lytic mixture, denaturation of the DNA, neutralization, rinsing, baking to fix the DNA onto the filter, and incubation in prehybridization buffer (in this case at 45° C. for four hours). LG20 was end labeled with $^{32}$P using T4 DNA kinase and hybridized to the filters at 45° C. overnight. The filters were then washed as previously described and subjected to autoradiography. Probe-positive plaques were grown up in liquid culture and further characterized.

For screening, RF DNA from probe-positive plaques was purified, restricted with SmaI and run on a 12% polyacrylamide gel. Clones containing the mutagenized region were identified by the presence of a 55 bp SmaI-SmaI restriction fragment. One such clone designated M13SmaGlyPtBm2 was used in subsequent constructions.

Modification of the diphtheria toxin secretory leader for fusion to other sequences and adaptation to expression vectors Mutagenesis of the Amino terminal end of the diphtheria toxin secretory leader.

1. In order to alter the amino terminal end of the diphtheria toxin secretory leader, the MspI fragment containing the secretory leader of the diphtheria toxin gene was cloned into M13MP18. Plasmid S1, which contains the 1454 bp MspI fragment in the ClaI site of pBR322 was digested with HindIII, phenol extracted and ethanol precipitated. M13MP18 was digested with HindIII, bapped to prevent self ligation, phenol extracted and ethanol precipitated. The two preparations were ligated together using T4 DNA ligase under sticky end conditions transduced into competent *E. coli* K12 strain DG98 and plated onto IPTG-Xgal containing plates as described above. White plaques were picked and and grown in liquid broth. RF DNA was purified from minicultures and screened by restriction analysis for the presence of the expected 1343 HindIII-HindIII band consisting of a 1337 bp HindIII-Msp fragment from the diphtheria toxin structural gene and a 6 bp ClaI-HindIII fragment from pBR322. The orientation was determined by restriction with EcoRI and ClaI which yielded 4 fragments for the desired construct: a 3704 bp ClaI-EcoRI vector fragment; a 2895 bp ClaI-ClaI vector fragment, a 1659 bp fragment consisting of a 1059 bp ClaI-HindIII fragment from the diphtheria toxin structural gene and a 600 bp HindIII-ClaI fragment from M13MP18; and a 335 bp fragment consisting of a 51 bp EcoRI-HindIII fragment from the M13MP18 polylinker, a 6 bp HindIII-ClaI fragment of pBR322 and a 278 bp MspI-ClaI fragment from the diphtheria toxin structural gene. One such construct was designated M13MspA2 and was used for subsequent mutagenesis.

2. The amino terminal end of the diphtheria toxin secretory leader was altered in the following manner:

a. The native GTG translation start codon was replaced by a ATG start codon.

b. A HindIII restriction site (AAGCTT) was inserted just prior to this start codon to permit cloning into the desired expression vectors.

To accomplish these alterations, the following 30-mer oligodeoxyribonucleotide (herein referred to as LG18) was synthesized:

```
native:    G GTA AGG GGA TAC GTT GTG AGC AGA AAA CT

LG18:   5' G GTA AGG GGA AAG CTT ATGAGCAGAAAACT 3'

MET ser arg lys leu

--- modified start codon

------- inserted HindIII site
```

Site directed mutagenesis of M13MspA2 was carried out in the same manner as described above for site directed mutagenesis of M13PsBm except that the 30-mer LG18 was used for the mutagenesis and probing. In addition, the prehybridization, hybridization and filter wash was done at 58° C. Probe-positive plaques were grown up in liquid broth overnight, and RF DNA purified from them and subject to restriction analysis. Restriction with a combination of HindIII and ClaI yielded the following fragments in clones which were properly mutagenized: a 4039 bp fragment consisting of a 3755 bp HindIII-ClaI vector fragment and a 284 bp ClaI-HindIII fragment of the diphtheria toxin fragment; a 2895 bp ClaI-ClaI vector fragment; a 945 bp ClaI-HindIII fragment where the HindIII site is the mutagenized restriction site; a 600 bp ClaI-HindIII vector fragment; and a 114 bp HindIII-HindIII diphtheria toxin fragment in which one of the HindIII sites is from the mutagenized region. Single stranded DNA was isolated from phage in the supernatant from candidates giving proper restriction patterns and the mutagenized region was sequenced using the Sanger technique, *Proc. Nat. Acad. Sci. (USA)*, 74:5463 (1977). One such clone was designated MspL7-8.

Mutagenesis of the carboxyl end of the diphtheria toxin secretory leader.

The carboxyl end of the diphtheria secretory leader was modified in two ways:

1. A restriction site (SacI) was added such that when the DNA was restricted with SacI and blunt ended with DNA Polymerase I Klenow fragment, the sequence would terminate at the end of the last codon in the leader. This would provide a convenient place for fusing the leader to other sequences.

2. A second restriction site (BamHI) distal to the SacI site to permit separation of the entire modified diphtheria secretory leader way from the remainder of the structural gene and allow cloning into plasmid vectors.

To accomplish this, the following oligonucleotide (hereinafter referred to as LG19) was designed and synthesized by standard techniques:

followed by treatment with DNA Polymerase I Klenow fragment in the presence of the 4 dXTP's, which blunt ends by removing 3' overhangs, the following sequence results:

```
5'... CA GCC CAT GCG     CGGATCCTGTTGTTGATTCTT... 3'
3'... GT CGG GTA CGC     GCCTAGGACAACAACTAAGAA... 5'
        ala  his  ala
```

Thus, fusion of this sequence to a sequence coding for a processed secreted protein, will align the secertory leader in-phase to that protein sequence.

Single stranded DNA from clone MspL7-8 was mutagenized with the 30-mer oligomer LG19 as was previously described with the following modifications. For the initial hybridization, the mixture of 10 picomoles of oligomer and 1 pmole of single stranded DNA was heated to 100° C. for three minutes, and then slowly cooled from 76° C. to 42° C. In the initial screening, the probe as hybridized to the filters at 55° C. overnight and the filter washes were done at 55° C. Following growth in liquid broth of probe-positive plaques, and isolation of RF DNA, confirmation of the expected alterations was accomplished by restriction analysis. The mutagenized clones gave a 1173 bp and a 7420 bp band when restricted with BamHI and run on a 1% agarose gel. Restriction with HindIII and SacI followed by electrophoresis on a 12.5% acrylamide gel resulted in the following restriction pattern: a 7205 bp HindIII-SacI vector band and a 1149 bp SacI-HindIII insert band where the SacI site is the added restriction site which could not be distinguished; a 114 bp HindIII-HindIII insert band; a 80 bp HindIII-SacI insert band, where the SacI site is the added restriction site; and a 45 bp SacI-HindIII vector band. Final confirmation was obtained by isolating single-stranded DNA from the phage in the supernatant and sequencing by the dideoxy method. One such construct used in later constructions was designated M13DTL7.

Cloning the modified diphtheria toxin secretory leader into a plasmid vector.

The now fully mutagenized diphtheria toxin secretory leader was separated from the remainder of the diphtheria toxin structural gene and cloned into pBR322. RF DNA purified from clone M13DTL7 was restricted with BamHI and HindIII yielding fragments

```
native:  CA GCC CAT GCA GGC GCT GAT GAT GTT GTT GAT TCT T

LG19:  5' CAGCCCATGCGAGC TCG GAT CCT GTT GTT GAT TCT T
           ser ala his ala
              ------- inserted SacI site
              -------- inserted BamHI site
```

The alanine is the last amino acid of the secretory leader and lies adjacent to the amino terminal end of the native diphtheria toxin protein sequence. By restriction with SacI which cuts as follows:

of 7220 bp, 1143 bp, 114 bp, 86 bp (the desired fragment) and 30 bp. Plasmid pBR322 was restricted with HindIII and BamHI bapped to prevent self-ligation. Following ligation of the two preparations together using T4

```
5'... CAGCCCATGCGAGCT       CGGATCCTGTTGTTGATTCTT... 3'
3'... GTCGGGTACGC       TCGAGCCTAGGACAACAACTAAGAA... 5'
```

DNA ligase, transformation into competent DG98 and plating on ampicillin agar plates, DNA from ampicillin-resistant clones was purified and subjected to restriction analysis. Restriction with HindIII and BamHI followed by electrophoresis on a 12.5% polyacrylamide gel yielded an insert fragment of 86 bp. Confirmation was obtained by restriction with both combinations of HindIII and SacI which yielded a 80 bp fragment and HindIII and ApaI which yielded a 58 bp fragment. One clone used in later constructs was designated pBRDTL10.

Fusion of the modified diphtheria toxin secretory leader to the modified amino terminal end of the mature Pseudomonas exotoxin A sequences Fusion of the modified diphtheria toxin secretory leader to the amino terminal end of the mature Pseudomonas exotoxin A sequence was accomplished using the newly introduced SacI restriction site of the leader and the SmaI of the exotoxin A sequence. This was accomplished by replacing a 71 bp region between the EcoRI site and mutagenized SamI site of M13SmaGlyPtBm2 (of Example II.B) with the 109 bp EcoRI-SamI fragment containing the modified diphtheria toxin secretory leader from pBRSTL10 (of Example III.C).

M13SmaGlyPtBm2 was restricted with SmaI and EcoRI and bapped to prevent self-ligation. Plasmid pBRDTL10 was restricted with SacI, and blunt-ended using 0.5 mM dXTP's and 6 units of DNA Polymerase I Klenow fragment at 37° C. for one hour. Following phenol extraction, the preparation was restricted with EcoRI. As previously described, this procedure had the following result:

a. restriction with SacI:

```
5'... CAGCCCATGCGAGCT          CGGATCC... 3'
3'... GTCGGGTACGC              TCGAGCCTAGG... 5'
``` b. blunt-ending with DNA Polymerase I Klenow fragment:

```
5'... CA GCC CAT GCG      CGGATCC ... 3'
3'... GT CGG GTA CGC      GCCTAGG ... 5'
       ser ala his ala
``` where the alanine codon is the last codon of the diphtheria toxin secretory leader. These two preparations were ligated together using T4 DNA ligase at 14° C. for three days and transfected into competent DG98. Several plaques were grown up in liquid broth, and their RF DNA purified and subjected to restriction analysis. Restriction with HindIII resulted in a large 7230 bp fragment consisting most of the M13MP18 vector and a smaller 1590 bp insert fragment. Confirmation was obtained by restricting with either: (1) ApaI alone, which gave a 1167 bp and a 7653 bp fragment; (2) BamHI, which linearized the constructs; (3) A combination of ApaI and BamHI, which gave a 7318 bp, a 1167 bp and a 335 bp fragment; (4) SalI alone, which gave a 7421 bp, a 834 bp and a 565 bp fragment; and (5) a combination of EcoRI and SalI, which gave a 7217 bp EcoRI-SalI vector fragment, a 834 bp SalI-SalI insert fragment, a 565 bp SalI-SalI fragment and a 204 bp fragment. Thus, the expected sequence at the fusion site is:

```
5'... CA GCC CAT GCG GGG GCC GAG GAA G ... 3'
3'... GT CGG GTA CGC CCC CGG CTC CTT C ... 5'
    ... ser ala his ala gly ala glu glu ala ...
```

DT toxin secretroy leader/---/ mature Pseudomonas toxin wherein --- is the inserted glycine codon.

One such candidate designated M13DTLPTBm 9 was used in later constructions.

Modification of the carboxyl end of the Pseudomonas exotoxin A gene to make more convenient for cloning In order to facilitate later piecing together of the entire Pseudomonas exotoxin A gene, the EcoRI site within the Pseudomonas sequence was removed and an XbaI site was added by stepwide constructions into available plasmids. The fragment encoding for the carboxyl end of Pseudomonas exotoxin A was then cloned into pCS3. pCS3 has been deposited in the American Type Culture Collection (ATCC) under the terms of the Budapest Treaty and has accession number 39142.

Removal of the EcoRI site within the Pseudomonas toxin sequence.

M13MP18 was restricted with BamHI, blunt-ended with DNA Polymerase I Klenow fragment and the 4 dXTP's, and bapped to prevent self-ligation. The plasmid carrying the Pseudomonas 1267 bp EcoRI-BglII fragment, psBglEco 2-1 (Example I.B), was restricted with EcoRI and SalI and blunt-ended with DNA Polymerase I Klenow fragment and the 4 dXTP's. The two DNA preparations were then ligated using T4 DNA ligase at 10° C. overnight, and transfected into competent DG98. Several plaques were grown up in liquid broth and their DNA purified. The proper clones containing the 1013 bp EcoRI-SalI fragment were identified by restriction analysis. Digestion with EcoRI and HindIII (both sites are within the M13MP18 polylinker, the EcoRI site of the fragment having been destoryed) resulted in a 7199 bp vector fragment and a 1072 bp fragment containing the insert. The inserted was oriented by digesting the candidates with PstI and BamHI which yielded a 7789 bp and a 482 bp fragment for the clones with the insert in the desired orientation. Single-stranded DNA was isolated from phage in the supernatant of the culture and the sequence across the BamHI/EcoRI junction determined by dideoxy sequencing. The sequence at the junction demonstrated the destruction of both the BamHI vector and EcoRI insert site:

```
5'... TATGAATTGATCC... 3'
```

In addition, this procedure added several restriction sites present in the polylinker (i.e., XbaI and SalI) to the Pseudomonas sequences 3' thereof. One such clone used in later constructions was designated M13PTOO-1-6.

Cloning of the altered carboxyl end Pseudomonas sequences into pOPDTerm.

The Pseudomonas exotoxin carboxyl end was placed into a temperature-sensitive copy-mutant plasmid by taking advantage of the homologous sticky ends of SalI and XhoI, which, when ligated together, destroy both sites. Plasmid pOPDterm was restricted with EcoRI and XhoI, and bapped to prevent self-ligation. RF DNA M13PTCOO-1-6 was restricted with EcoRI and SalI. The two preparations were ligated using T4 DNA ligase overnight at 14° C. To cut down the background further, the ligation mixture was restricted with BglII, which would only cut nonchimeric vector. The preparation was transformed into DG98 and plate on ampicillin plates at 30° C. Several drug-resistant clones were grown up in liquid broth, and their DNA isolated and subjected to restriction analysis. Restriction with the combination XbaI and EcoRI yielded a 1052 bp and a 4703 bp fragment. One such clone was designated pOPPTCOO-2-1.

Piecing back together the entire Pseudomonas exotoxin A structural gene.

In order to reconstruct the entire Pseudomonas exotoxin A structural gene, with the diphtheria toxin secretory leader replacing the native secretory leader, the M13DTLPTBm and pOPPTCOO-2 DNA's were used. Plasmid pOPPTCOO-2-1 was restricted with EcoRI and BamHI and treated with bacterial alkaline phosphatase to prevent self-ligation. RF M13DTLPTBm was restricted with EcoRI and BamHI. The two DNA preparations were mixed, and ligated using T4 DNA ligase. Following transformation into D698 and growth at 30° C., ampicillin resistant colonies were grown in broth culture, and their DNA isolated and subjected to restriction analysis. Restriction with the combination of EcoRI and BamHI yielded a 5178 bp and a 1594 bp restriction with XbaI and SalI yielded a 4911 bp, a 1024 bp, and a 837 bp fragment. One such construct was designated pOPWPT 2-11.

Inserting the $P_L$ promoter in front of the modified Pseudomonas exotoxin A gene.

The $P_L$ promoter DNA fragment was transferred from plasmid pPLOP to pOPWPT 2-11. pPLOP has been deposited under the terms of the Budapest Treaty in the ATCC under accession number 39,947. pPLOP was digested with HindIII, PstI and BamHI (the BamHI restriction was included to minimize self-ligation). pOPWPT 2-11 was digested with HindIII and PstI and treated with bacterial alkaline phosphatase to prevent self-ligation. The two DNA preparations were ligated using T4 DNA ligase at 14° C. overnight, transformed into DG95λcI857, plated onto ampicillin-containing plates and grown at 30° C. Drug resistant colonies were grown in liquid broth and their DNA purified and subjected to restriction mapping. Digestion with the combination of EcoRI and SalI resulted in a 5731 bp, a 837 bp and a 528 bp fragment. Digestion with XbaI and EcoRI resulted in 4707 bp and a 2389 bp fragment. Digestion with HindIII and XbaI resulted in a 5602 bp and a 2034 bp fragment. Digestion with EcoRI and HindIII resulted in a 6741 bp and a 355 bp fragment, confirming the presence of the $P_L$ promoter fragment. Digestion with the combination HindIII, XbaI and PstI resulted in a 3399 bp, a 2034 bp, and a 1663 bp fragment. Digestion with the combination HindIII, XbaI and PvuII yielded a 3056 bp, a 2034 bp, and a 2006 bp fragment. One final construct was labeled pPLOPDTLWPT 2-10. pPLOPDTLWPT 2-10 has been deposited in the ATCC under the terms of the Budapest Treaty under accession number 67,166.

Assessment of expression

General assessment of a protein of the expected molecular weight.

To look for the production of a protein of the expected molecular weight, the clone was inocculated into minimal media, and grown at 30° C. for two hours 20 minutes, followed by 42° C. for seven hours. The cells were harvested and resuspended in 1/28th volume of 10 mM Tris, 0.1 mM EDTA pH 8.0. 1.5% of the sample was run on a 12.5% SDS polyacrylamide gel stack along with native Pseudomonas toxin. A band of the expected molecular weight was detected relative to the migration of authentic Pseudomonas toxin bands run as a standard.

Detection of secretion of Pseudomonas exotoxin A from *E. coli*.

Figure 8:
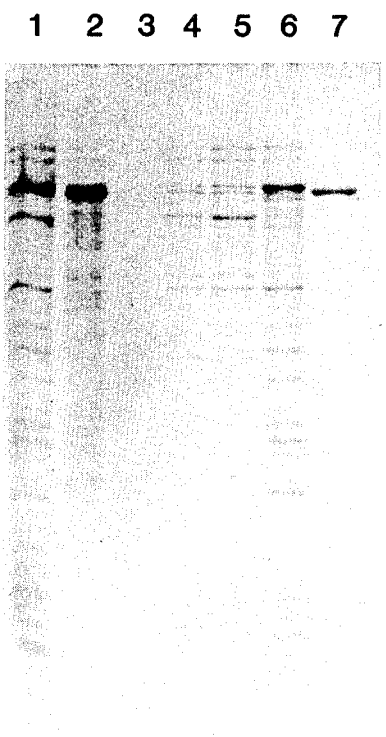
FIG. 8 is a gel showing the distribution of Pseudomonas toxin according to the invention in cells and culture medium.
Figure 7:
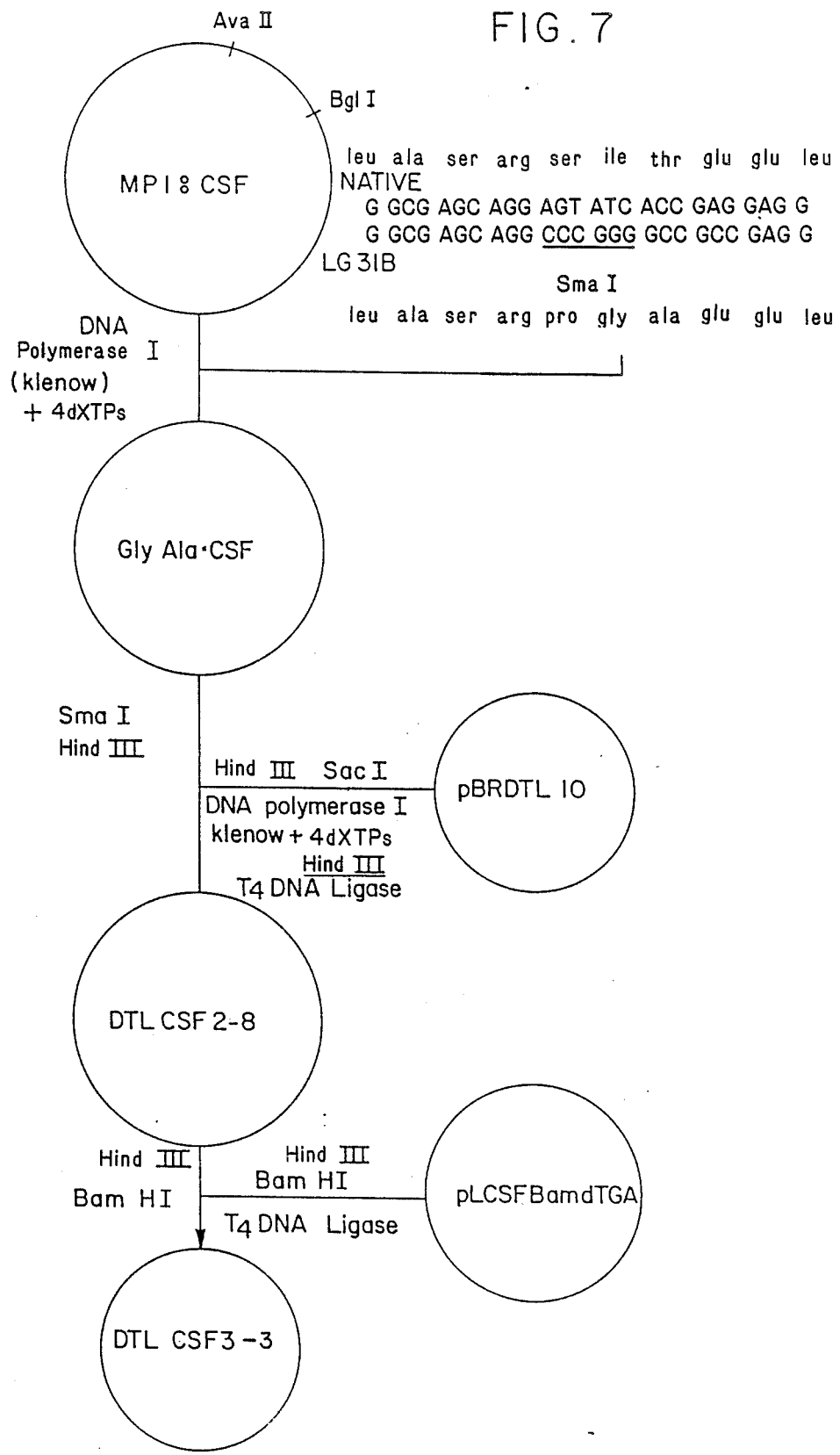
FIG. 7 is a schematic illustration of the construction of plasmids DTCCSF3-3.

Cells were inoculated into minimal media containing ampicillin, and grown at 30° C. for two hours followed by 42° C. for four hours. The cells were centrifuged and the supernatant was saved as "culture medium". The cell pellets were resuspended in 0.9 ml of 30 mM Tris pH 7.4, 20% sucrose, 1 mM EDTA. A small sample of this was saved as "total cells". To the resuspended cells was added lysozyme to a final concentration of 30 µg/ml and the mixture was incubated on ice for 30 minutes followed by centrifugation. The supernatant was saved as "periplasmic fraction". The pellets were resuspended in 0.8 ml of water and processed through 4 cycles of quick freezing and thawing. Following centrifugation, the supernatant was saved as "freeze thaw". The pellets were resuspended in SDS buffer by boiling. Each of the samples were run on a 12.5% SDS polyacrylamide gel stack along with native Pseudomonas exotoxin A. At least half of the material migrating with the expected molecular weights was found in the "culture medium" fraction. Some material was found in the "whole cell fraction" and some was found in the periplasmic fraction". The material found in the cell pellet had a predominant molecular weight suggestive of the nonprocessed form. Thus, it appears that the toxin is secreted out of the cell wall of *E. coli* in a soluble form. These results are showin in FIG. 8 in which "total cell" in lane 1; "culture medium" (1 ml) is lane 2; "culture medium" (20 λ) is lane 3; "periplasmic fraction" is lane 4; "freeze thaw" is lane 5; "membrane fraction" is lane 6; and "native purified PE toxin standard" is lane 7.

Determination of the enzymatic activity.

The enzymatic activity was determined for both the cell ssociated and secreted form of the toxin. For the cell associated form, the cell pellet was sonicated and in some cases boiled in SDS. The various fractions were serially diluted with the ADP-ribosylation activity was determined by standard means (see Greenfield et al., supra). The amount of toxin in the preparations was estimated by comparing to a standard on a Coomasie gel. Using this approximation, the ADP-ribosylation activity of the *E. coli* made product was in the same range as the native Pseudomonas produced product.

Determination of the biological activity.

The cytotoxicity of the product against the cell line MCF7 (a known target of Pseudomonas exotoxin A) was tested using the supernatant of several samples in the MTT assay. The amount of toxin in the preparations was estimated as above. Again, the biological activity of the *E. coli* made product was in the same range as the native Pseudomonas exotoxin A made in Pseudomonas. 0.1M for native PE TCID$_{50}$ in the MTT assay as compared to 0.05 nM for *E. coli* produced material according to the invention in the same assay.

Thus, the product made in *E. coli* appears to be processed, secreted out of the cell wall, soluble, enzymatically active and biologically active.

EXAMPLE 2

Construction of DTLCSF Clones

Mutagenesis of the amino terminal end of CSF to permit fusion to the DTL leader

The following oligonucleotide was used to mutagenize the amino terminal end of the CSF clone. It is labeled LG31B:

5'
GGCGAGCAGGCCCGGGGCCGAG-
GAGGT 3'

The sequence aligns up to the native sequence as follows:

```
         leu  ala  ser  arg  ser  ile  thr  glu  glu  val native:  G GCG AGC AGG AGT ATC ACC GAG GAG GT

LG31B:   G GCG AGC AGG CCC GGG GCC GAG GAG GT leu  ala  ser  arg  pro  gly  ala  glu  glu  val
                             -----------
                                SmaI
```

The native amino terminal end of the processed form of CSF-I is Glu Glu Val . . . . The oligonucleotide will add onto the amino terminal end of this sequence codons for glycine (GGG) and alanine (GCC). In addition, it will create a SmaI restriction site, which cuts blunt-ended between the CCC and GGG sequence, just prior to these added on codons.

The coding sequence for CSF-1 was cloned to M13MP18 as follows: pcCSF-17 (ATCC 53,149), which has been described in detail in U.S. patent application Ser. No. 876,819 filed June 20, 1986 and assigned to the assignee hereof, was digested with AvaI and BglII and blunt-ended with DNA Polymerase I Klenow fragment and dXTPs. XhoI linkers were added to the blunt-ends using T4 DNA ligase and ATP and the entire Xho-ended fragment was ligated into M13MP18 which had been previously digested with SalI and bapped. The resulting plasmid M13MP18 CSF was picked from transformed DG98 and identified by an appropriate CSF-1 specific probe.

10.8 pmoles of LG31B was hybridized with 3.08 µg of M13MP18 CSF, treated with 6 units of DNA Polymerase I large fragment (Klenow) and 0.5 mMdXTPs at room temperature for one hour 20 minutes and transformed into DG98. The transformation mixture was plated onto a lawn of DG98, grown overnight at 37° C. and probed with the oligomer as follows. Plaques were lifted onto nitrocellulose filters, dried, washed for 10 minutes with 0.2% triton X-100, 50 mM Tris, 62.5 mM EDTA, denatured for 10 minutes in 500N NaOH, 1.0M NaCl, neutralized for 10 minutes with 500 mM tris pH 8.0, 1.0M NaCl, and rinsed for 10 minutes with 300 mM NaCl, 10 mM Tris, pH 7.6, 1 mM EDTA. Following baking under a vacuum at 80° C. for four hours, the filters were treated with prehybridization buffer (6×SSC, 0.1% SDS, 5×Denhardt's solution, 50 mM NaP, pH 7.0, and 126 µg/ml sonicated denatured calf thymus DNA) for four hours at 57° C. For labeling the probe, 36 pmoles of LG31 was treated with 32P-ATP and T4 DNA kinase at 37° C. and the unincorporated label was removed by running over a Biogel P-4 TM 1 cc spin column. For the hybridization, 9 pmoles of the labeled probe in 20 mls of hybridization buffer (same as the prehybridization buffer except that the carrier DNA was at a concentration of 10 µg/ml), was added to the filter. Following incubation at 57° C. for 16 hours, the filters were washed twice in 5×SSC, 0.1% SDS at 53° C. for 30 minutes, followed by a 30 minute wash in 2×SSC, 0.1% SDS at 53° C. The filters were then dried, and autoradiographed. Probe positive plaques were picked and used to infect DG98 overnight at 37° C. These were labeled H3CSF or GlyAlaCSF.

For confirmation, DNA was isolated from the individual clones and subjected to restriction analysis using SmaI and EcoRI restriction enzymes, followed by electrophoresis on a 1% agarose gel. Further confirmation was obtained by restricting with SmaI alone, EcoRI alone, and a combination of SmaI and EcoRI. Additional confirmation was obtained by restricting with EcoRI and HindIII, HindIII and XbaI, or SmaI and HindIII. One such clone, GlyAlaCSF-1, was pursued further.

Fusion of the mutagenized amino terminal end of CSF-1 to the Mutagenized DTL

For the fusion, DNA from GlyAlaCSF-1 clone was restricted with SmaI and HindIII, phenol extracted, ethanol precipitated, resuspended in 10 mM Tris, 0.1 mM EDTA, pH 8.0 and run over a Biogel P-4 spin column. The vector consisted of pBRDTL10 was restricted with SacI and blunt-ended followed by treatment with bacterial alkaline phosphatase in the following manner. pBRDTL10 was restricted with SacI, phenol extracted, ethanol precipitated, resuspended in 10 mM Tris, 1 mM EDTA pH 8.0 followed by running over a 1 cc Biogel P-4 spin column. The preparation was then blunt-ended by treatment with DNA Polymerase I large fragment (Klenow fragment) and all 4 dXTP's at room temperature for one hour followed by phenol extraction and desalting on a biogel P-4 spin column. It was then restricted with HindIII treated with bacterial alkaline phosphatase, phenol extracted, ethanol precipitated, resuspended in 120 mM Tris 0.1 mM EDTA pH 8 and desalted by running over a Biogel P-4 spin column. The two DNA preparations were mixed, ligated using T4 DNA ligase at 10° C. for 16 hours, transformed into DG98 and plated onto ampicillin containing plates. For identification of the desired construct, ampicillin-resistant clones were grown up, DNA isolated from them and subjected to restriction analysis using either EcoRI, BamHI, or PstI restriction enzymes. One construction, termed DTLCSF2-8 was pursued further.

Final Construction of Expression Vector for DTL CSF

For construction of an expression vector, DTLCSF2-8 and pLCSFBamdTGA were used. pLCSFBamdTGA (ATCC 67,144 which has been described in detail in U.S. patent application Ser. No. 876,819 filed June 20, 1986 and assigned to the assignee hereof) was made as follows: Plasmid pcCSF-17 was digested with restriction endonucleases to exuse the coding sequence of CSF-1 and was ligated using T4 DNA ligase into M13MP18 which has been digested using the same restriction endonuclease. A synthetic oligodeoxyribonucleotide which had the sequence 5'-GAGG-GATCCTGATCACCGCAGGTCC-3', was purified and hybridized to the M13MP18-clone carrying the coding sequence CSF-1 by treatment with DNA Polymerase I large fragment (Klenow) on dXTPs at room temperature. Following hybridiation, the mixture is used to transform E. coli strain DG98 and probed with the same oligomer labeled with $^{32}\gamma P$ with T4 DNA kinase. The resulting plasmid designated pCSF-BamBcl results in a new BCL site at codons 159–160. To make pCSF-BamdTGA in which the codons 3' to the 159 stop codon are deleted. pCSF-BamBcl was digested with XhoI and BclI and ligated using T4 DNA ligase into pCSF-1 which had been previously digested with XhoI and BamHI. Plasmid pCSF-BamdTGA is confirmed by reisolating the plasmid and restriction fragment analysis showing the loss of the Bam site.

To construct pLCSFBamdTGA, plasmid pFC54.t (ATCC 39,789) which contains the $P_L$ promoter and the *Bacillus thuringiensis* positive retroregulatory sequence, described in EPO Application Publication No. 217,331, published Mar. 29, 1985, was digested with HindIII and BamHI and blunt-ended with DNA Polymerase Klenow large fragment and dXTPs. pCSM-BamdTGA was digested and HindIII and EcoRI and blunt-ended the two digests were mixed and ligated using T4 DNA ligase. Plasmid pLCSFBamdTGA was confirmed by restriction fragment analysis.

pLCSFBamdTGA was restricted with HindIII and BamHI, phenol extracted, ethanol precipitated and desalted over a Biogel P-4 spin column. DTLCSF2-8 was restricted with HindIII and BamHI, treated with bacterial alkaline phosphatase, phenol extracted, ethanol precipitated and desalted over a Biogel P-4 spin column. The two DNA preparations were ligated together using T4 DNA ligase at 10° C. for 72 hours, transformed into DG116, plated onto ampicillin containing plates and grown overnight at 30° C. Overnight cultures were grown from drug-resistant colonies, DNA isolated from them and subjected to DNA restriction analysis in order to identify the desired construct. The proper construction was identified by restriction with a combination of BamHI and HindIII and confirmed by restriction with the combination ApaI and BamHI, or BamHI and HindIII.

Expression

For expression, cultures were grown in N-8 supplemented with 0.5% glucose, 0.01 mM FeSO4, 0.5% casamino acids and 100 µg/ml ampicillin at 30° C. for four hours followed by induction by growth at 42° C. for six hours. Cells were harvested by centrifugation, resuspended in 1/50th volume of 10 mM Tris, 0.1 mM EDTA, pH 8.0 and sonicated for three minutes. Secretion into the media was checked by TCA precipitating protein from 1 ml of media. Samples were run on a 15% SDS polyacrylamide gel with stack and the gels were either stained using coummassie or transferred to cyanogen bromide paper which was then probed with anti G1 antibody and I125 Staph A protein. Clones DTLCSF 3-3, 3-9, 3-10, 3-12 and 3-13 gave a band on Coomasie staining which had the expected molecular weight of a fully processed form of CSF. In addition, this band reacted with the anti-G1 antibody.

The following is a list of plasmids deposited in the ATCC relating to the present invention the ATCC is located at 12301 Parklawn Drive, Rockville, Md. 20852-1776.

| Plasmid | Deposit Date | Accession No. |
| --- | --- | --- |
| pLCSFBamdTGA | 6/19/86 | 67,144 |
| pCS3 | 6/3/82 | 39,142 |
| pPLOP | 12/18/84 | 39,947 |
| E. coli strain D698 | 7/13/84 | 39,768 |
| pPLOPDTLWP | 7/25/86 | 67,166 |

These deposits were made under the provisions of the Budapest Treaty on the International Recognition of the Deposit of Microorganisms for the Purposes of Patent Procedure and the Regulations thereunder (Budapest Treaty). This assures maintenance of a viable culture for 30 years from date of deposit. The deposits will be made available by ATCC under the terms of the Budapest Treaty, and subject to an agreement between applicants and ATCC which assures permanent and unrestricted availability upon issuance of the pertinent U.S. patent. The assignee herein agrees that if the culture on deposit die or be lost or destroyed when cultivated under suitable conditions, it will be promptly replaced upon notification with a viable speciment of the same culture. Availability of the deposits is not to be construed as a license to practice the invention in contravention of the rights granted under the authority of any government in accordance with its patent laws.

These deposits were made for the convenience of the relevant public and do not constitute an admission that a written description would not be sufficient to permit practice of the invention or an intention to limit the invention to these specific constructs. Set forth hereinabove is a complete written description enabling a practitioner of ordinary skill to duplicate the constructs deposited and to construct alternative forms of DNA, or organisms containing it, which permit practice of the invention as claimed.

The scope of the invention is not to be construed as limited by the illustrative embodiments set forth herein, but is to be determined in accordance with the appended claims.

What is claimed is:

1. DNA comprising a DNA sequence encoding a mature protein heterologous to a DT leader sequence with an NH2 terminal consensus sequence comprising about 7 amino acids having substantial homology to the first 7 amino terminal amino acids of mature DT wherein said mature protein is Pseudomonas exotoxin A having a glycine NH2-terminal in addition to the coding sequence of Pseudomonas exotoxin A.

2. The DNA sequence of claim 1 wherein said Pseudomonas exotoxin A has the NH2-terminal sequence gly-ala-glu-glu-ala-phe-asp.

3. The DNA sequence of claim 8 wherein said mature protein is CSF-1 having gly-ala NH2-terminal in addition to the coding sequence of mature CSF-1.

4. The DNA sequence of claim 3 wherein said mature protein is CSF-1 having the NH2-terminal sequence gly-ala-glu-glu-val.

5. An expression vector comprising a DNA sequence encoding the DT leader sequence in reading frame with the DNA sequence of claim 1.

6. An expression vector comprising a DNA sequence encoding the DT leader sequence in reading frame with the DNA sequence of claim 3.

7. The expression vector of claim 5 wherein the DNA sequence encoding the $NH_2$-terminal acid of the DT leader is ATG.

8. The expression vector of claim 6 wherein the DNA sequence encoding the $NH_2$-terminal amino acid sequence of the DT leader is ATG.

9. A host organism transformed with the expression vector of claim 5.

10. A host organism transformed with the expression vector of claim 6.

11. A host organism transformed with the expression vector of claim 7.

12. A host organism transformed with the expression vector of claim 8.

* * * * *